United States Patent
Murphy et al.

(10) Patent No.: US 10,519,207 B2
(45) Date of Patent: Dec. 31, 2019

(54) COMPOSITIONS AND METHODS FOR TREATING OPIOID TOLERANCE

(71) Applicant: GEORGIA STATE UNIVERSITY RESEARCH FOUNDATION, INC., Atlanta, GA (US)

(72) Inventors: Anne Z. Murphy, Atlanta, GA (US); Lori Eidson, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/735,672

(22) PCT Filed: Jun. 13, 2016

(86) PCT No.: PCT/US2016/037177
§ 371 (c)(1),
(2) Date: Dec. 12, 2017

(87) PCT Pub. No.: WO2016/201409
PCT Pub. Date: Dec. 15, 2016

(65) Prior Publication Data
US 2018/0362607 A1    Dec. 20, 2018

Related U.S. Application Data

(60) Provisional application No. 62/175,158, filed on Jun. 12, 2015.

(51) Int. Cl.
*A61K 38/19* (2006.01)
*C07K 14/525* (2006.01)
*A61K 47/60* (2017.01)
*A61K 31/135* (2006.01)

(52) U.S. Cl.
CPC .......... *C07K 14/525* (2013.01); *A61K 38/191* (2013.01); *A61K 47/60* (2017.08); *A61K 31/135* (2013.01); *C07K 2319/60* (2013.01)

(58) Field of Classification Search
None
See application file for complete search history.

(56) References Cited

U.S. PATENT DOCUMENTS

| 4,179,337 A | 12/1979 | Davis et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 5,215,743 A | 6/1993 | Singh et al. |
| 5,219,740 A | 6/1993 | Miller et al. |
| 5,576,201 A | 11/1996 | Mason et al. |
| 5,766,883 A | 6/1998 | Balance et al. |
| 5,833,948 A | 11/1998 | Tournier et al. |
| 5,876,969 A | 3/1999 | Fleer et al. |
| 7,446,174 B2 | 11/2008 | Desjarlais et al. |
| 7,662,367 B2 | 2/2010 | Desjarlais et al. |
| 2007/0009477 A1 | 1/2007 | Desjarlais et al. |
| 2007/0172449 A1 | 7/2007 | Carmichael et al. |
| 2012/0088713 A1 | 4/2012 | Lane et al. |

FOREIGN PATENT DOCUMENTS

| EP | 2335731 A2 | 6/2011 |
| EP | 2371859 A2 | 10/2011 |
| WO | 1997027212 A1 | 7/1997 |
| WO | 1997027213 A1 | 7/1997 |
| WO | 2004046346 A3 | 7/2004 |
| WO | 2006/113487 A1 | 10/2006 |
| WO | 2015/051337 A2 | 4/2015 |

OTHER PUBLICATIONS

Wells, 1990, Biochemistry 29:8509-8517.*
Ngo et al., 1994, The Protein Folding Problem and Tertiary Structure Prediction, pp. 492-495.*
Anderson et al., "Human gene therapy" Science 256:808-813 (1992).
Ashkenazi et al., "Immunoadhesins as research tools and therapeutic agents" 1997, Curr Opin Immunol 9:195-200.
Babcock, et al., "Hedgehog Signaling Regulates Nociceptive Sensitization", Curr Biol. 21:8, 2011, 1525-1533.
Bachtell R, et al., "Targeting the Toll of Drug Abuse: The Translational Potential of Toll-Like Receptor 4" (2015) CNS Neurol Disord Drug Targets 14:692-699.
Basbaum AI, et al. Endogenous pain control mechanisms: Review and hypothesis (1978) Ann Neurol 4:451-462.
Bett et al. "Packaging Capacity and Stability of Human Adenovirus Type 5 Vectors" (1993) J. Virol. 67:5911-5921.
Brower, V. "Naked DNA vaccines come of age" Nature Biotechnology, 16:1304-1305 (1998).
Cearley et al., "Expanded repertoire of AAV vector serotypes mediate unique patterns of transduction in mouse brain" Molecular Therapy, 16:1710-1718, 2008.
Chamow et al., "Immunoadhesins: principles and applications" 1996, Trends Biotechnol 14:52-60.
DeLeo JA, et al. "Neuroimmune activation and neuroinflammation in chronic pain and opioid tolerance/hyperalgesia" (2004) Neuroscientist 10:40-52.
Dowell D, et al al. "CDC Guideline for Prescribing Opioids for Chronic Pain" (2016) MMWR Recomm Rep 65:1-49.
Dzau et al., "Gene therapy for cardiovascular disease" Trends in Biotechnology 11:205-210 (1993).
Eidson LN, et al. "Blockade of Toll-Like Receptor 4 Attenuates Morphine Tolerance and Facilitates the Pain Relieving Properties of Morphine" (2013) J Neurosci 33:15952-15963.
Gulur P, et al. "Opioid tolerance—a predictor of increased length of stay and higher readmission rates" (2014) Pain Physician 17:E503-507.

(Continued)

*Primary Examiner* — Christine J Saoud
*Assistant Examiner* — Jon M Lockard
(74) *Attorney, Agent, or Firm* — Meunier Carlin & Curfman LLC

(57) ABSTRACT

The present disclosure is directed to a method of treating morphine tolerance and/or symptoms associated therewith by administration to a subject in need thereof a DN-TNF polypeptide that inhibits the activity of soluble TNF- but not transmembrane TNF-α.

9 Claims, 14 Drawing Sheets

Specification includes a Sequence Listing.

(56) References Cited

OTHER PUBLICATIONS

Fine SM, et al. "Tumor Necrosis Factor α Inhibits Glutamate Uptake by Primary Human Astrocytes Implications for Pathogenesis of HIV-1 Dementia" (1996) J Biol Chem 271:15303-15306.
Fingl et al., In: The Pharmacological Basis of Therapeutics, Ch. 1 (1975).
Haj-Ahmad and Graham "Development of a helper-independent human adenovirus vector and its use in the transfer of the herpes simplex virus thymidine kinase gene." (1986) J. Virol. 57:267-274.
Hargreaves K, et al. "A new and sensitive method for measuring thermal nociception in cutaneous hyperalgesia" (1988) Pain 32:77-88.
Hutchinson MR, et al. "Opioid-Induced Glial Activation: Mechanisms of Activation and Implications for Opioid Analgesia, Dependence, and Reward" (2007) ScientificWorldJournal 7:98-111.
Hutchinson MR, et al. "Proinflammatory cytokines oppose opioid-induced acute and chronic analgesia" (2008) Brain Behav Immun 22:1178-1189.
International Search Report and Written Opinion issued in the related International Application No. PCT/US2016/037177 dated Sep. 15, 2016.
Kanai Y, et al. "The elusive transporters with a high affinity for glutamate." (1993) Trends Neurosci 16:365-370.
Kosek E, et al. Evidence of different mediators of central inflammation in dysfunctional and inflammatory pain—Interleukin-8 in fibromyalgia and interleukin-1 β in rheumatoid arthritis (2015) J Neuroimmunol 280:49-55.
Kriegler M, et al. "A novel form of TNF/cachectin is a cell surface cytotoxic transmembrane protein: ramifications for the complex physiology of TNF" (1988) Cell 53:45-53.
Kinstler et al, "Mono-N-terminal poly (ethylene glycol)—protein conjugates" Advanced Drug Deliveries Reviews, 54, 477-485 (2002).
Lau BK, et al. "Descending modulation of pain: the GABA disinhibition hypothesis of analgesia" (2014) Curr Opin Neurobiol 29C:159-164.
Loyd DR, et al. (2008) "Sexually dimorphic activation of the periaqueductal gray-rostral ventromedial medullary circuit during the development of tolerance to morphine in the rat" Eur J Neurosci 27:1517-1.
Mann et al. "Construction of a retrovirus packaging mutant and its use to produce helper-free defective retrovirus" (1983) Cell 33:153-159.
Marchetti L, et al. "Tumor Necrosis Factor (TNF)-mediated Neuroprotection against Glutamate-induced Excitotoxicity Is Enhanced by N-Methyl-D-aspartate Receptor Activation" (2004) J Biol Chem 279:32869-32881.
McCoy MK, et al. "Intranigral lentiviral delivery of dominant-negative TNF attenuates neurodegeneration and behavioral deficits in hemiparkinsonian rats" (2008) Mol Ther 16:1572-1579.
McLemore GL, et al. "The effects of LY293558, an AMPA receptor antagonist, on acute and chronic morphine dependence" (1997) Brain Res 778:120-126.
Nakagawa T, et al. "Inhibition of morphine tolerance and dependence by MS-153, a glutamate transporter activator" (2001) Eur J Pharmacol 419:39-45.
Ogoshi F, et al. "Tumor necrosis-factor-alpha (TNF-α) induces rapid insertion of $Ca^{2+}$-permeable α-amino-3-hydroxyl-5-methyl-4-isoxazole-propionate (AMPA)/kainate (Ca-A/K) channels in a subset of hippocampal pyramidal neurons" (2005) Exp Neurol 193:384-393.
Pasternak GW, et al. "Mu Opioids and Their Receptors: Evolution of a Concept" (2013) Pharmacol Rev 65:1257-1317.
Peterson PK, et al. "The opioid-cytokine connection" (1998) J Neuroimmunol 83:63-69.
Raghavendra V, et al."The Role of Spinal Neuroimmune Activation in Morphine Tolerance/Hyperalgesia in Neuropathic and Sham-Operated Rats" (2002) J Neurosci 22:9980-9989.
Roberts, M J et al, "Chemistry for peptide and protein PEGylation" Advanced Drug Delivery Reviews, 54, 459-476 (2002).
Rothstein JD, et al. "Knockout of glutamate transporters reveals a major role for astroglial transport in excitotoxicity and clearance of glutamate" (1996) Neuron 16:675-686.
Seror R, et al. "Pattern of demyelination occurring during anti-TNF-α therapy: a French national survey" (2013) Rheumatology (Oxford) 52:868-874.
Seth et al. "Mechanism of enhancement of DNA expression consequent to cointernalization of a replication-deficient adenovirus and unmodified plasmid DNA." (1994) J. Virol. 68:933-940.
Shen CH, et al. "Etanercept Restores the Antinociceptive Effect of Morphine and Suppresses Spinal Neuroinflammation in Morphine-Tolerant Rats" (2011) Anesth Analg 112:454-459).
Shen CH, et al. "Intrathecal etanercept partially restores morphine's antinociception in morphine-tolerant rats via attenuation of the glutamatergic transmission" (2011) Anesth Analg 113:184-190.
Shen, et al., "Role of neuroinflammation in morphine tolerance: effect of tumor necrosis factor-α", Acta Anaesthesiologica Taiwanica 50, 2012, 178-182.
Steed PM, et al. "Inactivation of TNF signaling by rationally designed dominant-negative TNF variants" (2003) Science 301:1895-1898.
Stellwagen D, et al. "Differential Regulation of AMPA Receptor and GABA Receptor Trafficking by Tumor Necrosis Factor-α" (2005) J Neurosci 25:3219-3228.
Sun J, et al. "Transgene-mediated expression of tumor necrosis factor soluble receptor attenuates morphine tolerance in rats" (2012) Gene Ther 19:101-108.
Tai YH, et al. "Amitriptyline suppresses neuroinflammation and up-regulates glutamate transporters in morphine-tolerant rats" (2006) Pain 124:77-86.
Trujillo KA, et al. "Inhibition of morphine tolerance and dependence by the NMDA receptor antagonist MK-801" (1991) Science 251:85-87.
Vaughan CW, et al. "How opioids inhibit GABA-mediated neurotransmission" (1997) Nature 390:611-614.
Von Maltzan K, et al. "Investigation of the Role of TNF-a Converting Enzyme (TACE) in the Inhibition of Cell Surface and Soluble TNF-a Production by Acute Ethanol Exposure" (2012) PLoS One 7:e29890.
Wagner et al., "Transferrin-polycation conjugates as carriers for DNA uptake into cells" Proc. Natl. Acad. Sci. U.S.A. 87:3410-3414 (1990).
Wang X, et al. "Morphine activates neuroinflammation in a manner parallel to endotoxin" (2012) Proc Natl Acad Sci U S A 109:6325-6330.
Watkins LR, et al. "Glia: novel counter-regulators of opioid analgesia" (2005) Trends Neurosci 28:661-669.
Wong CS, et al. "Loss of intrathecal morphine analgesia in terminal cancer patients is associated with high levels of excitatory amino acids in the CSF" (2002) Can J Anaesth 49:561-565.
Wu et al., "Receptor-mediated in vitro gene transformation by a soluble DNA carrier system." J. Biol. Chem. 262:4429-4432 (1987).
Zamecnik et al., "Inhibition of replication and expression of human T-cell lymphotropic virus type III in cultured cells by exogenous synthetic oligonucleotides complementary to viral . . . " Proc. Natl. Acad. Sci. U.S.A. 83:4143-4146 (1986).
Zalevsky J, et al. "Dominant-negative inhibitors of soluble TNF attenuate experimental arthritis without suppressing innate immunity to infection" (2007) J Immunol 179:1872-1883.
Extended European Search Report issued for European Application No. 16808504, dated Oct. 22, 2018, 9 pages.
Jhala S.S., et al., "Thiamine deficiency results in release of soluble factors that disrupt mitochondrial membrane potential and downregulate the glutamate transporter splice-variant GLT-1b in cultured astrocytes.", Send to Biochem Biophys Res Commun. Jun. 6, 2014;448(3):335-41. doi: 10.1016/j.bbrc.2014.04.017. Epub Apr. 13, 2014.
Database Geneseq [Online] Jan. 26, 2006, "Human TNF-alpha variant XENP268" XP-002785135, retrieved from EBI accession No. GSP: AED95319, 2 pages.

(56) References Cited

OTHER PUBLICATIONS

Shen CH, et al., "Role of neuroinflammation in morphine tolerance: effect of tumor necrosis factor-α", Acta Anaesthesiologica Taiwanica 50(4), 2012, 178-182.

* cited by examiner

SEQUENCE LISTING

```
<160> NUMBER OF SEQ ID NOS: 3

<210> SEQ ID NO 1
<211> LENGTH: 495
<212> TYPE: DNA
<213> ORGANISM: Artificial Sequence
<220> FEATURE:
<223> OTHER INFORMATION: Synthetic Construct

<400> SEQUENCE: 1
atgcaccacc accaccaca cgtacgctcc tcctcccgca ctccgtccga caaaccggta     60
gctcacgtag tagctaaccc gcaggctgaa ggtcagctgc agtggctgaa ccgccgcgct    120
aacgctctgc tggctaacgg tgtagaactg cgcgacaacc agctggtagt accgtccgaa    180
ggtctgtacc tgatctactc ccaggtactg ttcaaaggtc agggttgtcc gtccactcac    240
gtactgctga ctcacactat ctcccgcatc gctgtatcct accagactaa agtaaacctg    300
ctgtccgcta tcaaatcccc gtgtcagcgc gaaactccgg aaggtgctga agctaaaccg    360
tggtacgaac cgatctacct gggtggtgta ttccagctgg aaaaaggtga ccgcctgtcc    420
gctgaaatca accgcccgga ctacctggac ttcgctgaat ccggtcaggt atacttcggt    480
atcatcgctc tgtga                                                    495

<210> SEQ ID NO 2
<211> LENGTH: 164
<212> TYPE: PRT
<213> ORGANISM: Artificial Sequence
```

<220> FEATURE:
<223> OTHER INFORMATION: Synthetic Construct

<400> SEQUENCE: 2

Met His His His His His Val Arg Ser Ser Arg Thr Pro Ser
1               5                   10                  15

Asp Lys Pro Val Ala His Val Val Ala Asn Pro Gln Ala Glu Gly Gln
            20                  25                  30

Leu Gln Trp Leu Asn Arg Arg Ala Asn Ala Leu Leu Ala Asn Gly Val
        35                  40                  45

Glu Leu Arg Asp Asn Gln Leu Val Val Pro Ser Glu Gly Leu Tyr Leu
    50                  55                  60

Ile Tyr Ser Gln Val Leu Phe Lys Gly Gln Gly Cys Pro Ser Thr His
65                  70                  75                  80

Val Leu Leu Thr His Thr Ile Ser Arg Ile Ala Val Ser Tyr Gln Thr
                85                  90                  95

Lys Val Asn Leu Leu Ser Ala Ile Lys Ser Pro Cys Gln Arg Glu Thr
            100                 105                 110

Pro Glu Gly Ala Glu Ala Lys Pro Trp Tyr Glu Pro Ile Tyr Leu Gly
        115                 120                 125

Gly Val Phe Gln Leu Glu Lys Gly Asp Arg Leu Ser Ala Glu Ile Asn
    130                 135                 140

Arg Pro Asp Tyr Leu Asp Phe Ala Glu Ser Gly Gln Val Tyr Phe Gly
145                 150                 155                 160

Ile Ile Ala Leu

<210> SEQ ID NO 3
<211> LENGTH: 157
<212> TYPE: PRT
<213> ORGANISM: Artificial Sequence
<220> FEATURE:
<223> OTHER INFORMATION: Synthetic construct

<400> SEQUENCE: 3

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

COMPOSITIONS AND METHODS FOR TREATING OPIOID TOLERANCE

CROSS-REFERENCE TO RELATED APPLICATIONS

This application is a national stage application filed under 35 U.S.C. § 371 of PCT/US2016/037177 filed Jun. 13, 2016, which claims benefit of U.S. Provisional Application No. 62/175,158, filed Jun. 12, 2015, each of which is hereby incorporated herein by reference in its entirety.

STATEMENT REGARDING FEDERALLY SPONSORED RESEARCH OR DEVELOPMENT

This invention was made with Government Support under Grant No. DA016272 awarded by the National Institutes of Health. The Government has certain rights in the invention.

BACKGROUND

Opioid therapy remains a common strategy for severe and chronic pain management with 3-4% of adults in the U.S. receiving long-term opioid therapy (Dowell D, et al. (2016) MMWR Recomm Rep 65:1-49). However, decreased analgesic efficacy over time (i.e., tolerance) significantly impedes treatment for approximately 60% of the patient population (Gulur P, et al. (2014) Pain Physician 17:E503-507). Long-term opioid therapy is associated with increased risk of abuse, dependence, and dose-related fatal overdose (Dowell D, et al. (2016) MMWR Recomm Rep 65:1-49) Immune signaling is a significant contributor to the negative consequences of opioid therapy including tolerance, hyperalgesia, addiction, dependence, and withdrawal (Hutchinson M R, et al. (2007) ScientificWorldJournal 7:98-111), and has been implicated as a driving factor in a variety of chronic pain syndromes, including Rheumatoid arthritis (RA) and fibromyalgia (Heo Y J, et al. (2011) Arthritis Res Ther 13:R113; Kosek E, et al. (2015) J Neuroimmunol 280:49-55).

Currently, morphine tolerance is treated by ibudilast (AV411), minocycline, fluorocitrate, propentofylline. However, these immunomodulatory drugs have widespread and non-specific effects. Thus, significant drawbacks exist with the use of current treatments.

Understanding the mechanisms underlying opioid-induced neuroinflammation is paramount to developing effective pain management strategies that minimize the risk of dependence, abuse, and long-term consequences of chronic neuroinflammation.

SUMMARY

In contrast to the prior art, principles of the present disclosure provide a method of treating opioid tolerance and/or symptoms associated therewith comprising administering a therapeutically effective amount of a TNFα inhibitor, a glial inhibitor, or a combination thereof to a subject in need thereof, whereby said symptoms are improved in said subject. In some embodiments, the opioid is morphine. In some embodiments, the TNFα inhibitor is a dominant negative TNF-α inhibitor. In some embodiments, the dominant negative inhibitor is XPro1595.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic of lenti-GFP and lenti-DN-TNF lentiviral vectors. Both lenti-GFP and lenti-DN-TNF vectors contain a chicken β-actin cytomegalovirus enhancer/promoter (CAG), β-globin intron, a central polypurine tract of HIV-1 (ppt), a woodchuck hepatitis virus post-transciptional response element (WPRE), and a self-inactivating deletion in the 3' LTR. The lenti-DN-TNF vector contains an internal ribosome entry site (IRES) for GFP expression following the sequence for pro-human DN-TNF (A145R/I97T). FIG. 1B shows paw withdrawal latency (s) during nociceptive testing on day 1 (D1) and day 3 (D3) at baseline and 15 minutes post saline or morphine injection in groups pretreated with lenti-GFP or lenti-DN-TNF; Lenti-GFP+Saline (n=4; black circles), lenti-DN-TNF+Saline (n=5; black squares) lenti-GFP+Morphine (n=10; red circles), and lenti-DN-TNF+Morphine (n=10; red squares). FIG. 1C shows representative locations of lenti-GFP (circles) and lenti-DNTNF (squares) microinfusions in the caudal vlPAG (Bregma −8.03), and representative light and FITC images of injection location and GFP expression from the same section. Dotted lines delineate cerebral aqueduct. FIG. 1D shows paw withdrawal latency (s) during cumulative morphine injections on day 4 to assess for tolerance. FIG. 1E shows representative locations of lenti-GFP (circles) and lenti-DN-TNF (squares) microinfusions in the vlPAG (Bregma −8.04), and representative FITC photomicrograph of GFP expression in the vlPAG. Aq indicates the location of the aqueduct. FIG. 1F shows paw withdrawal latency (s) during cumulative morphine injections in rats pretreated with lenti-GFP+PAG Saline (n=4; black circles), lenti-GFP+PAG LPS (n=4; gray circles), lenti-DN-TNF+PAG Saline (n=6; black squares), and lenti-DN-TNF+PAG LPS (n=9; gray squares).

FIGS. 2A, 2C, and 2E are representative photomicrographs (left inset) of specific hybridization in the caudal PAG (Bregma −8.04) and bar graph of mean specific hybridization signal for GLT-1 (FIG. 2A), GLAST (FIG. 2C), and neuronal EAAC1 (FIG. 2E) in the caudal vlPAG of rats treated with lenti-GFP+Saline and lenti-GFP+Morphine (right). FIGS. 2B, 2D, and 2F are representative photomicrographs (left inset) of specific hybridization and bar graph showing mean specific hybridization for GLT-1 (FIG. 2B), GLAST (FIG. 2D), and neuronal EAAC1 (FIG. 2F) in the caudal PAG (Bregma −8.04) of rats treated with lenti-GFP+PAG Saline (left) and lenti-GFP+PAG LPS (right). Specific hybridization is reported as the mean disintegrations per minute per milligram of tissue (dpm/mg)±SEM; n=4/6 per group). Aq delineates cerebral aqueduct and the black box represents the sampling region.

FIG. 3A shows paw withdrawal latency (s) during nociceptive testing on day 1 (D1) and day 3 (D3) at baseline and 15 minutes post saline or morphine injection in groups pre-treated with XPro1595 or Vehicle (saline); Vehicle+Saline (n=8; black circles), XPro+Saline (n=8; black squares), Vehicle+Morphine (n=11; gray circles), and XPro1595+Morphine (n=11; gray squares). FIG. 3B shows paw withdrawal latency (s) during cumulative morphine injections on day 4. Data are represented as mean paw withdrawal latency ±SEM.

FIG. 4F show all primer pairs produced amplicons of appropriate size as compared to the control DNA ladder. Representative schematic of vlPAG tissue punch location (top left). PCR amplicons from each gene of interest were run on a 2% agarose gel (main photomicrograph) to demonstrate primer specificity. All genes localized to regions appropriate to their predicted size.

DETAILED DESCRIPTION

Figure 1A:
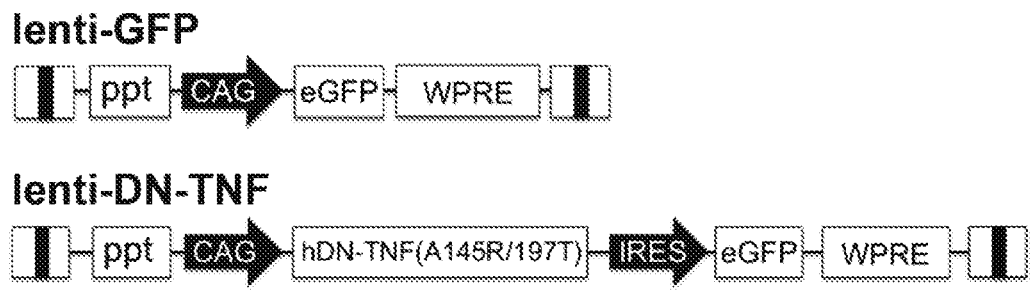
FIGS. 1A to 1F show viral vector-mediated sequestration of soluble TNF in the vlPAG prevents the development of tolerance to systemic morphine and to LPS microinfusion into the vlPAG.

Although significant efforts to identify effective therapies for the treatment of morphine tolerance and/or symptoms associated therewith have been undertaken, to date there is a dearth of such therapies. As such, there is a significant need to develop effective therapies to prevent or treat morphine tolerance and/or symptoms associated therewith.

One such strategy is described herein. Tumor necrosis factor (TNF) is a pleiotropic cytokine important in the regulation of numerous physiological and pathological processes such as inflammation, autoimmunity, neurodegeneration, neuroprotection, demyelination and remyelination. There are two active forms of TNF, soluble-TNF (solTNF) and transmembrane-TNF (tmTNF) whose biological responses are primarily mediated by two distinct receptors TNFR1 and TNFR2, respectively. TNFR1 has a death domain and signaling through this receptor has been implicated in both neuronal and oligodendrocyte death whereas signaling through TNFR2 has been implicated in neuroprotection and remyelination. It has recently been demonstrated that systemic delivery of a selective inhibitor of solTNF, XPro1595, which binds solTNF forming inactive heterodimers, significantly improves functional recovery, reduces axonal damage and promotes remyelination in experimental autoimmune encephalomyelitis (EAE), an animal model of multiple sclerosis. In contrast, inhibition of solTNF and tmTNF with the non-specific TNF inhibitor, etanercept (decoy TNFR2 which blocks solTNF, tmTNF and lymphotoxin), proved neither therapeutic nor neuroprotective in EAE.

Moreover, as disclosed herein, treatment with TNF inhibitors effectively improved functional outcome in a model of morphine tolerance. In some embodiments, selective soluble TNF-α inhibitors and non-selective TNF-α inhibitors both improved functional outcome in a model of morphine tolerance. In some embodiments, however, the two classes of inhibitors provided for differential effects and functional outcomes in the morphine tolerance model. In one embodiment the non-selective anti-TNF drug etanercept restores the ability of morphine to acutely inhibit tail flick reflex in morphine tolerant animals, however, etanercept has not been coadministered chronically with morphine, and the ability of etanercept to preserve morphine analgesia has not been tested.

Accordingly, principles of the present disclosure provide compositions and methods for treating morphine tolerance and/or symptoms associated therewith. The methods comprise administering to a patient in need thereof an inhibitor of TNF-α. In some embodiments, the methods comprise administering to a patient in need thereof an inhibitor of TNF-α that inhibits signaling of soluble TNF-α but not transmembrane TNF-α. In some embodiments, the inhibitor is a dominant negative inhibitor of soluble TNF-α. In some embodiments, the dominant negative inhibitor of TNF-α is XPro1595.

By morphine tolerance is meant decreased efficacy as a function of repeated use over time, resulting in dose escalation.

By symptoms associated with or caused by morphine tolerance is meant higher doses of the drug is required to achieve the same analgesic effect.

Inhibitors of TNF-α

In some embodiments inhibitors of TNFα may be non-selective inhibitors, such as, but not limited to etanercept, infliximab, adalimumab and the like. Preferred inhibitors of TNFα may be dominant negative TNFα proteins, referred to herein as "DNTNF-α," "DN-TNF-α proteins," "TNFα variants," "TNFα variant proteins," "variant TNF-α," "variant TNF-α," and the like. By "variant TNF-α" or "TNF-α proteins" is meant TNFα or TNF-α proteins that differ from the corresponding wild type protein by at least 1 amino acid. The following is a nucleic acid sequence of human TNF-α—an additional six histidine codons, located between the start codon and the first amino acid, are underlined:

(SEQ ID NO: 1)

```
  1  atgcaccacc accaccacca cgtacgctcc tcctcccgca ctccgtccga caaaccggta
 61  gctcacgtag tagctaaccc gcaggctgaa ggtcagctgc agtggctgaa ccgccgcgct
121  aacgctctgc tggctaacgg tgtagaactg cgcgacaacc agctggtagt accgtccgaa
181  ggtctgtacc tgatctactc ccaggtactg ttcaaaggtc agggttgtcc gtccactcac
```

```
-continued
241   gtactgctga ctcacactat ctcccgcatc gctgtatcct accagactaa agtaaacctg 301   ctgtccgcta tcaaatcccc gtgtcagcgc gaaactccgg aaggtgctga agctaaaccg 361   tggtacgaac cgatctacct gggtggtgta ttccagctgg aaaaaggtga ccgcctgtcc 421   gctgaaatca accgcccgga ctacctggac ttcgctgaat ccggtcaggt atacttcggt 481   atcatcgctc tgtga.
```

Thus, a variant of human TNF-α can be compared to SEQ ID NO:1 DN-TNF-α proteins are disclosed in detail in U.S. Pat. No. 7,446,174, which is incorporated herein in its entirety by reference. As used herein variant TNF-α or TNF-α proteins include TNF-α monomers, dimers or trimers. Included within the definition of "variant TNF-α" are competitive inhibitor TNF-α variants. While certain variants as described herein, one of skill in the art will understand that other variants may be made while retaining the function of inhibiting soluble but not transmembrane TNF-α.

Thus, the proteins of the invention are antagonists of wild type TNF-α. By "antagonists of wild type TNF-α" is meant that the variant TNF-α protein inhibits or significantly decreases at least one biological activity of wild-type TNF-α.

In a preferred embodiment the variant is antagonist of soluble TNF-α, but does not significantly antagonize transmembrane TNF-α, e.g., DN-TNF-α protein as disclosed herein inhibits signaling by soluble TNF-α, but not transmembrane TNF-α. By "inhibits the activity of TNF-α" and grammatical equivalents is meant at least a 10% reduction in activity relative to wild-type, soluble TNF-α, more preferably at least a 50% reduction in activity relative to wild-type, soluble TNF-α activity, and even more preferably, at least 90% reduction in activity relative to wild-type, soluble TNF-α activity. Preferably there is an inhibition in wild-type soluble TNF-α activity in the absence of reduced signaling by transmembrane TNF-α. In a preferred embodiment, the activity of soluble TNF-α is inhibited while the activity of transmembrane TNF-α is substantially and preferably completely maintained.

The TNF proteins of the invention have modulated activity as compared to wild type proteins. In a preferred embodiment, variant TNF-α proteins exhibit decreased biological activity (e.g. antagonism) as compared to wild type TNF-α, including but not limited to, decreased binding to a receptor (p55, p75 or both), decreased activation and/or ultimately a loss of cytotoxic activity. By "cytotoxic activity" herein refers to the ability of a TNF-α variant to selectively kill or inhibit cells. DN variants of TNF-α proteins that exhibit less than 50% biological activity as compared to wild type are preferred. More preferred are DN variants of TNF-α proteins that exhibit less than 25%, even more preferred are variant proteins that exhibit less than 15%, and most preferred are DN variants of TNF-α proteins that exhibit less than 10% of a biological activity of wild-type TNF-α. Suitable assays include, but are not limited to, caspase assays, TNF-α cytotoxicity assays, DNA binding assays, transcription assays (using reporter constructs), size exclusion chromatography assays and radiolabeling/immuno-precipitation), and stability assays (including the use of circular dichroism (CD) assays and equilibrium studies), according to methods know in the art.

In one embodiment, at least one property critical for binding affinity of the variant TNF-α proteins is altered when compared to the same property of wild type TNF-α and in particular, variant TNF-α proteins with altered receptor affinity are preferred. Particularly preferred are variants of TNF-α with altered affinity toward oligomerization to wild type TNF-α. Thus, the invention provides variant TNF-α proteins with altered binding affinities such that the variant TNF-α proteins will preferentially oligomerize with wild type TNF-α, but do not substantially interact with wild type TNF receptors, i.e., p55, p75. "Preferentially" in this case means that given equal amounts of variant TNF-α monomers and wild type TNF-α monomers, at least 25% of the resulting trimers are mixed trimers of variant and wild type TNF-α, with at least about 50% being preferred, and at least about 80-90% being particularly preferred. In other words, it is preferable that the variant TNF-α proteins of the invention have greater affinity for wild type TNF-α protein as compared to wild type TNF-α proteins. By "do not substantially interact with TNF receptors" is meant that the variant TNF-α proteins will not be able to associate with either the p55 or p75 receptors to significantly activate the receptor and initiate the TNF signaling pathway(s). In a preferred embodiment, at least a 50% decrease in receptor activation is seen, with greater than 50%, 76%, 80-90% being preferred.

In some embodiments, the variants of the invention are antagonists of both soluble and transmembrane TNF-α. However, as described herein, preferred variant TNF-α proteins are antagonists of the activity of soluble TNF-α but do not substantially affect the activity of transmembrane TNF-α. Thus, a reduction of activity of the heterotrimers for soluble TNF-α is as outlined above, with reductions in biological activity of at least 10%, 25, 50, 75, 80, 90, 95, 99 or 100% all being preferred. However, some of the variants outlined herein comprise selective inhibition; that is, they inhibit soluble TNF-α activity but do not substantially inhibit transmembrane TNF-α. In these embodiments, it is preferred that at least 80%, 85, 90, 95, 98, 99 or 100% of the transmembrane TNF-α activity is maintained. This may also be expressed as a ratio; that is, selective inhibition can include a ratio of inhibition of soluble to transmembrane TNF-α. For example, variants that result in at least a 10:1 selective inhibition of soluble to transmembrane TNF-α activity are preferred, with 50:1, 100:1, 200:1, 500:1, 1000:1 or higher find particular use in the invention. Thus one embodiment utilizes variants, such as double mutants at positions 87/145 as outlined herein, that substantially inhibit or eliminate soluble TNF-α activity (for example by exchanging with homotrimeric wild-type to form heterotrimers that do not bind to TNF-α receptors or that bind but do not activate receptor signaling) but do not significantly affect (and preferably do not alter at all) transmembrane TNF-α activity. Without being bound by theory, the variants exhibiting such differential inhibition allow the decrease of opioid tolerance without a corresponding loss in immune response, demyelination of neurons, or other side effects of inhibitors of transmembrane TNF-α activity.

In one embodiment, the affected biological activity of the variants is the activation of receptor signaling by wild type TNF-α proteins. In a preferred embodiment, the variant TNF-α protein interacts with the wild type TNF-α protein such that the complex comprising the variant TNF-α and wild type TNF-α has reduced capacity to activate (as outlined above for "substantial inhibition"), and in preferred embodiments is incapable of activating, one or both of the TNF receptors, i.e. p55 TNF-R or p75 TNF-R. In a preferred embodiment, the variant TNF-α protein is a variant TNF-α protein which functions as an antagonist of wild type TNF-α. Preferably, the variant TNF-α protein preferentially interacts with wild type TNF-α to form mixed trimers with the wild type protein such that receptor binding does not significantly occur and/or TNF-α signaling is not initiated. By mixed trimers is meant that monomers of wild type and variant TNF-α proteins interact to form heterotrimeric TNF-α. Mixed trimers may comprise 1 variant TNF-α protein:2 wild type TNF-α proteins, 2 variant TNF-α proteins:1 wild type TNF-α protein. In some embodiments, trimers may be formed comprising only variant TNF-α proteins.

The variant TNF-α antagonist proteins of the invention are highly specific for TNF-α antagonism relative to TNF-beta antagonism. Additional characteristics include improved stability, pharmacokinetics, and high affinity for wild type TNF-α. Variants with higher affinity toward wild type TNF-α may be generated from variants exhibiting TNF-α antagonism as outlined above.

Similarly, variant TNF-α proteins, for example are experimentally tested and validated in in vivo and in in vitro assays. Suitable assays include, but are not limited to, activity assays and binding assays. For example, TNF-α activity assays, such as detecting apoptosis via caspase activity can be used to screen for TNF-α variants that are antagonists of wild type TNF-α. Other assays include using the Sytox green nucleic acid stain to detect TNF-induced cell permeability in an Actinomycin-D sensitized cell line. As this stain is excluded from live cells, but penetrates dying cells, this assay also can be used to detect TNF-α variants that are agonists of wild-type TNF-α. By "agonists of "wild type TNF-α" is meant that the variant TNF-α protein enhances the activation of receptor signaling by wild type TNF-α proteins. Generally, variant TNF-α proteins that function as agonists of wild type TNF-α are not preferred. However, in some embodiments, variant TNF-α proteins that function as agonists of wild type TNF-α protein are preferred. An example of an NF kappaB assay is presented in Example 7 of U.S. Pat. No. 7,446,174, which is expressly incorporated herein by reference.

In a preferred embodiment, binding affinities of variant TNF-α proteins as compared to wild type TNF-α proteins for naturally occurring TNF-α and TNF receptor proteins such as p55 and p75 are determined. Suitable assays include, but are not limited to, e.g., quantitative comparisons comparing kinetic and equilibrium binding constants, as are known in the art. Examples of binding assays are described in Example 6 of U.S. Pat. No. 7,446,174, which is expressly incorporated herein by reference.

In a preferred embodiment, the variant TNF-α protein has an amino acid sequence that differs from a wild type TNF-α sequence by at least 1 amino acid, with from 1, 2, 3, 4, 5, 6, 7, 8, 9 and 10 amino acid changes or more all being contemplated. Expressed as a percentage, the variant TNF-α proteins of the invention preferably are greater than 90% identical to wild-type, with greater than 95, 97, 98 and 99% all being contemplated. The following is an amino acid sequence for human TNF-α (SEQ ID NO:2) with an additional 6 histidines (underlined) between the start codon and the first amino acid.

```
                                             (SEQ ID NO: 2)
MHHHHHHVRS SSRTPSDKPV AHVVANPQAE GQLQWLNRRA

NALLANGVEL RDNQLVVPSE GLYLIYSQVL FKGQGCPSTH

VLLTHTISRI AVSYQTKVNL LSAIKSPCQR ETPEGAEAKP

WYEPIYLGGV FQLEKGDRLS AEINRPDYLD FAESGQVYFG

IIAL.
```

Stated differently, based on the human TNF-α sequence of FIG. 1B (SEQ ID NO:2), variant TNF-α proteins have at least about 1 residue that differs from the human TNF-α sequence, with at least about 2, 3, 4, 5, 6, 7 or 8 variant residues. Preferred variant TNF-α proteins have 3 to 8 variant residues. As will be evident to one of skill in the art the sequence in SEQ ID NO:2 includes an N-terminal 6 His tag.

Table 1 below shows the positions and amino acid changes in certain TNF-α variants.

TABLE 1

| Wild-type TNF amino acid | Wild-type TNF amino acid number | Mutants created |
|---|---|---|
| Q | 21 | R |
| N | 30 | D |
| R | 31 | I, D, E |
| R | 32 | D, E, S |
| A | 33 | E |
| A | 35 | S |
| K | 65 | D, T, M, W, I, Q, S, N, V, E |
| G | 66 | Q, K |
| Q | 67 | D, W, Y, R, K, S |
| A | 111 | R, E |
| K | 112 | D, E |
| Y | 115 | Q, K, E, N, R, F, H, M, L, I, W, D, T, S |
| D | 140 | R, K |
| D | 143 | E, N, Q, S, R, K |
| F | 144 | N |
| A | 145 | R, D, K, N, H, T, Q, E, Y, M, S, F |
| E | 146 | N, K, R, S |
| S | 147 | R |

Also made double mutants K65E/D143K, K65E/D143R, K65D/D143K, and K65D/D143R

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

TNF-α proteins may be fused to, for example, to other therapeutic proteins or to other proteins such as Fc or serum albumin for therapeutic or pharmacokinetic purposes. In this embodiment, a TNF-α protein of the present invention is operably linked to a fusion partner. The fusion partner may be any moiety that provides an intended therapeutic or pharmacokinetic effect. Examples of fusion partners include but are not limited to Human Serum Albumin, a therapeutic agent, a cytotoxic or cytotoxic molecule, radionucleotide, and an Fc, etc. As used herein, an Fc fusion is synonymous with the terms "immunoadhesin", "Ig fusion", "Ig chimera", and "receptor globulin" as used in the prior art (Chamow et al., 1996, *Trends Biotechnol* 14:52-60; Ashkenazi et al., 1997, *Curr Opin Immunol* 9:195-200, both incorporated by reference). An Fc fusion combines the Fc region of an immunoglobulin with the target-binding region of a TNF-α protein, for example. See for example U.S. Pat. Nos. 5,766,883 and 5,876,969, both of which are incorporated by reference.

In a preferred embodiment, the variant TNF-α proteins comprise variant residues selected from the following positions 21, 23, 30, 31, 32, 33, 34, 35, 57, 65, 66, 67, 69, 75, 84, 86, 87, 91, 97, 101, 111, 112, 115, 140, 143, 144, 145, 146, and 147. Preferred amino acids for each position, including the human TNF-α residues, are shown in FIG. 2. Thus, for example, at position 143, preferred amino acids are Glu, Asn, Gln, Ser, Arg, and Lys; etc. Preferred changes include: V1M, Q21C, Q21 R, E23C, R31C, N34E, V91E, Q21R, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R. These may be done either individually or in combination, with any combination being possible. However, as outlined herein, preferred embodiments utilize at least 1 to 8, and preferably more, variant amino acid positions in each variant TNF-α protein.

In an additional aspect, the invention provides TNF-α variants selected from the group consisting of XENP268 XENP344, XENP345, XENP346, XENP550, XENP551, XENP557, XENP1593, XENP1594, and XENP1595 as outlined in Example 3 OF U.S. Pat. No. 7,662,367, which is incorporated herein by reference.

In an additional aspect, the invention provides methods of forming a TNF-α heterotrimer in vivo in a mammal comprising administering to the mammal a variant TNF-α molecule as compared to the corresponding wild-type mammalian TNF-α, wherein said TNF-α variant is substantially free of agonistic activity.

In an additional aspect, the invention provides methods of screening for selective inhibitors comprising contacting a candidate agent with a soluble TNF-α protein and assaying for TNF-α biological activity; contacting a candidate agent with a transmembrane TNF-α protein and assaying for TNF-α biological activity, and determining whether the agent is a selective inhibitor. The agent may be a protein (including peptides and antibodies, as described herein) or small molecules.

In a further aspect, the invention provides variant TNF-α proteins that interact with the wild type TNF-α to form mixed trimers incapable of activating receptor signaling. Preferably, variant TNF-α proteins with 1, 2, 3, 4, 5, 6 and 7 amino acid changes are used as compared to wild type TNF-α protein. In a preferred embodiment, these changes are selected from positions 1, 21, 23, 30, 31, 32, 33, 34, 35, 57, 65, 66, 67, 69, 75, 84, 86, 87, 91, 97, 101, 111, 112, 115, 140, 143, 144, 145, 146 and 147. In an additional aspect, the non-naturally occurring variant TNF-α proteins have substitutions selected from the group of substitutions consisting of V1M, Q21C, Q21R, E23C, N34E, V91E, N30D, R31C, R311, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R.

In another preferred embodiment, substitutions may be made either individually or in combination, with any combination being possible. Preferred embodiments utilize at least one, and preferably more, positions in each variant TNF-α protein. For example, substitutions at any of positions 31, 57, 69, 75, 86, 87, 97, 101, 115, 143, 145, and 146 may be combined to form double variants. In addition triple, quadruple, quintuple and the like, point variants may be generated.

In one aspect the invention provides TNF-α variants comprising the amino acid substitutions A145R/I97T. In one aspect, the invention provides TNF-α variants comprising the amino acid substitutions V1M, R31C, C69V, Y87H, C101, and A145R. In a preferred embodiment, this variant is PEGylated and is referred to as "XPro1595" herein.

In a preferred embodiment the variant is XPro1595, a PEGylated protein comprising V1M, R31C, C69V, Y87H, C101, and A145R mutations relative to the wild type human sequence.

For purposes of the present invention, the areas of the wild type or naturally occurring TNF-α molecule to be modified are selected from the group consisting of the Large Domain (also known as II), Small Domain (also known as I), the DE loop, and the trimer interface. The Large Domain, the Small Domain and the DE loop are the receptor interaction domains. The modifications may be made solely in one of these areas or in any combination of these areas. The Large Domain preferred positions to be varied include: 21, 30, 31, 32, 33, 35, 65, 66, 67, 111, 112, 115, 140, 143, 144, 145, 146 and/or 147. For the Small Domain, the preferred positions to be modified are 75 and/or 97. For the DE Loop, the preferred position modifications are 84, 86, 87 and/or 91. The Trimer Interface has preferred double variants including positions 34 and 91 as well as at position 57. In a preferred embodiment, substitutions at multiple receptor interaction and/or trimerization domains may be combined. Examples include, but are not limited to, simultaneous substitution of amino acids at the large and small domains (e.g. A145R and I97T), large domain and DE loop (A145R and Y87H), and large domain and trimerization domain (A145R and L57F). Additional examples include any and all combinations, e.g., I97T and Y87H (small domain and DE loop). More specifically, theses variants may be in the form of single point variants, for example K112D, Y115K, Y115I, Y115T, A145E or A145R. These single point variants may be combined, for example, Y115I and A145E, or Y115I and A145R, or Y115T and A145R or Y115I and A145E; or any other combination.

Preferred double point variant positions include 57, 75, 86, 87, 97, 115, 143, 145, and 146; in any combination. In addition, double point variants may be generated including L57F and one of Y115I, Y115Q, Y115T, D143K, D143R, D143E, A145E, A145R, E146K or E146R. Other preferred double variants are Y115Q and at least one of D143N, D143Q, A145K, A145R, or E146K; Y115M and at least one of D143N, D143Q, A145K, A145R or E146K; and L57F and at least one of A145E or 146R; K65D and either D143K or D143R, K65E and either D143K or D143R, Y115Q and any of L75Q, L57W, L57Y, L57F, I97R, I97T, S86Q, D143N, E146K, A145R and I97T, A145R and either Y87R or Y87H; N34E and V91E; L75E and Y115Q; L75Q and Y115Q; L75E and A145R; and L75Q and A145R.

Further, triple point variants may be generated. Preferred positions include 34, 75, 87, 91, 115, 143, 145 and 146. Examples of triple point variants include V91 E, N34E and one of Y115I, Y115T, D143K, D143R, A145R, A145E E146K, and E146R. Other triple point variants include L75E and Y87H and at least one of Y115Q, A145R, Also, L75K, Y87H and Y115Q. More preferred are the triple point variants V91E, N34E and either A145R or A145E.

Variant TNF-α proteins may also be identified as being encoded by variant TNF-α nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred. In a preferred embodiment, a variant TNF-α nucleic acid encodes a variant TNF-α protein. As will be appreciated by those in the art, due to the degeneracy of the genetic code, an extremely large number of nucleic acids may be made, all of which encode the variant TNF-α proteins of the present invention. Thus, having identified a particular amino acid sequence, those skilled in the art could make any number of different nucleic acids, by simply modifying the sequence of one or more codons in a way which does not change the amino acid sequence of the variant TNF-α.

In one embodiment, the nucleic acid homology is determined through hybridization studies. Thus, for example, nucleic acids which hybridize under high stringency to the nucleic acid sequence shown in FIG. 1B (SEQ ID NO:2) or its complement and encode a variant TNF-α protein is considered a variant TNF-α gene. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), incorporated by reference. Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra. In addition, nucleic acid variants encode TNF-α protein variants comprising the amino acid substitutions described herein. In one embodiment, the TNF-α variant encodes a polypeptide variant comprising the amino acid substitutions A145R/I97T. In one aspect, the nucleic acid variant encodes a polypeptide comprising the amino acid substitutions V1M, R31C, C69V, Y87H, C101, and A145R, or any 1, 2, 3, 4 or 5 of these variant amino acids.

The variant TNF-α proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments. The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1A (SEQ ID NO:1) also includes the complement of the sequence. By the term "recombinant nucleic acid" is meant nucleic acid, originally formed in vitro, in general, by the manipulation of nucleic acid by endonucleases, in a form not normally found in nature. Thus an isolated variant TNF-α nucleic acid, in a linear form, or an expression vector formed in vitro by ligating DNA molecules that are not normally joined, are both considered recombinant for the purposes of this invention. By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild-type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant TNF-α protein from one organism in a different organism or host cell. Alternatively, the protein may be made at a significantly higher concentration than is normally seen, through the use of a inducible promoter or high expression promoter, such that the protein is made at increased concentration levels. Furthermore, all of the variant TNF-α proteins outlined herein are in a form not normally found in nature, as they contain amino acid substitutions, insertions and deletions, with substitutions being preferred, as discussed below.

Also included within the definition of variant TNF-α proteins of the present invention are amino acid sequence variants of the variant TNF-α sequences outlined herein and shown in the Figures. That is, the variant TNF-α proteins may contain additional variable positions as compared to human TNF-α. These variants fall into one or more of three classes: substitutional, insertional or deletional variants.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Using the nucleic acids of the present invention which encode a variant TNF-α protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant TNF-α protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the variant TNF-α protein, a replacement of the naturally occurring secretory leader sequence is desired. In this embodiment, an unrelated secretory leader sequence is operably linked to a variant TNF-α encoding nucleic acid leading to increased protein secretion. Thus, any secretory leader sequence resulting in enhanced secretion of the variant TNF-α protein, when compared to the secretion of TNF-α and its secretory sequence, is desired. Suitable secretory leader sequences that lead to the secretion of a protein are known in the art. In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from Bacillus are preferably used to express the fusion protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used. A preferred expression vector system is a retroviral vector system such as is generally described in PCT/US97/01019 and PCT/US97/01048, both of which are hereby incorporated by reference. In a preferred embodiment, the expression vector comprises the components described above and a gene encoding a variant TNF-α protein. As will be appreciated by those in the art, all combinations are possible and accordingly, as used herein, the combination of components, comprised by one or more vectors, which may be retroviral or not, is referred to herein as a "vector composition".

A number of viral based vectors have been used for gene delivery. See for example U.S. Pat. No. 5,576,201, which is expressly incorporated herein by reference. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors. Retroviral vectors can be constructed using techniques well known in the art. See, e.g., U.S. Pat. No. 5,219,740; Mann et al. (1983) *Cell* 33:153-159.

Adenovirus based systems have been developed for gene delivery and are suitable for delivery according to the methods described herein. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro.

Adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) *J. Virol.* 57:267-274; Bett et al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) BioTechniques 6:616-629; Rich et al. (1993) *Human Gene Therapy* 4:461-476.

In a preferred embodiment, the viral vectors used in the subject methods are AAV vectors. By an "AAV vector" is meant a vector derived from an adeno-associated virus serotype, including without limitation, AAV-1, AAV-2, AAV-3, AAV-4, AAV-5, AAVX7, etc. Typical AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. An AAV vector includes at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. For more on various AAV serotypes, see for example Cearley et al., *Molecular Therapy,* 16:1710-1718, 2008, which is expressly incorporated herein in its entirety by reference.

AAV expression vectors may be constructed using known techniques to provide as operatively linked components in the direction of transcription, control elements including a transcriptional initiation region, the DNA of interest and a transcriptional termination region. The control elements are selected to be functional in a thalamic and/or cortical neuron. Additional control elements may be included. The resulting construct which contains the operatively linked components is bounded (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) *Human Gene Therapy* 5:793-801; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

Suitable DNA molecules for use in AAV vectors will include, for example, a gene that encodes a protein that is defective or missing from a recipient subject or a gene that encodes a protein having a desired biological or therapeutic effect (e.g., an enzyme, or a neurotrophic factor). The artisan of reasonable skill will be able to determine which factor is appropriate based on the neurological disorder being treated.

The selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

Once made, the TNF-α protein may be covalently modified. For instance, a preferred type of covalent modification of variant TNF-α comprises linking the variant TNF-α polypeptide to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337, incorporated by reference. These nonproteinaceous polymers may also be used to enhance the variant TNF-α's ability to disrupt receptor binding, and/or in vivo stability. In another preferred embodiment, cysteines are designed into variant or wild type TNF-α in order to incorporate (a) labeling sites for characterization and (b) incorporate PEGylation sites. For example, labels that may be used are well known in the art and include but are not limited to biotin, tag and fluorescent labels (e.g. fluorescein). These labels may be used in various assays as are also well known in the art to achieve characterization. A variety of coupling chemistries may be used to achieve PEGylation, as is well known in the art. Examples include but are not limited to, the technologies of Shearwater and Enzon, which allow modification at primary amines, including but not limited to, lysine groups and the N-terminus. See, Kinstler et al, Advanced Drug Deliveries Reviews, 54, 477-485 (2002) and M J Roberts et al, Advanced Drug Delivery Reviews, 54, 459-476 (2002), both hereby incorporated by reference.

In one preferred embodiment, the optimal chemical modification sites are 21, 23, 31 and 45, taken alone or in any combination. In an even more preferred embodiment, a TNF-α variant of the present invention includes the R31C mutation.

In a preferred embodiment, the variant TNF-α protein is purified or isolated after expression. Variant TNF-α proteins may be isolated or purified in a variety of ways known to those skilled in the art depending on what other components are present in the sample.

Treatment Methods

The terms "treatment", "treating", and the like, as used herein include amelioration or elimination of a disease or condition once it has been established or alleviation of the characteristic symptoms of such disease or condition. A method as disclosed herein may also be used to, depending on the condition of the patient, prevent the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition.

Combination Treatments:

There are no specific therapies in use clinically to reverse morphine tolerance. Previous research in rodents suggested that drugs targeting the NMDA receptor may attenuate tolerance, however therapeutics targeted toward dampening NMDAR signaling have not yielded promising results clinically. Recent studies have also suggested that drugs targeting tyrosine kinases such as platelet-derived growth factor receptor-β (PDGFR-β), including the cancer drug Gleevec, may eliminate tolerance, but these are still in preliminary research stages. Morphine tolerance is typically circumvented by changing the type of opioid used for pain management. Thus, there exists a need for developing therapeutic strategies to better treat morphine tolerance and/or symptoms associated therewith. As described herein, DN-TNFs that inhibit soluble but not transmembrane TNF-α find use in treating morphine tolerance and/or symptoms associated therewith. These molecules find particular use when combined with currently available morphine tolerance therapies as known in the art and as described herein.

Formulations

Depending upon the manner of introduction, the pharmaceutical composition may be formulated in a variety of ways. The concentration of the therapeutically active variant TNF-α protein in the formulation may vary from about 0.1 to 100 weight %. In another preferred embodiment, the concentration of the variant TNF-α protein is in the range of 0.003 to 1.0 molar, with dosages from 0.03, 0.05, 0.1, 0.2, and 0.3 millimoles per kilogram of body weight being preferred.

The pharmaceutical compositions of the present invention comprise a variant TNF-α protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. In a preferred embodiment the formulation is as described in U.S. Pre-Grant Publication US20120088713, which is expressly incorporated herein by reference. For instance, the formulation comprises between 5 mg/ml and 500 mg/ml of a TNF inhibitor polypeptide; between 10 mM and 25 mM of a phosphate or citrate buffer; between 5% and 10% of a carbohydrate; and optionally NaCl, wherein the combined ionic strength of the buffer and the optional salt is an equivalent ionic strength of between 0.1M and 0.2M NaCl, wherein the formulation has a pH of between 6 and 7, is fluid at room temperature and at 37°, and has a viscosity of 10 centipoise or less at room temperature. 23

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, hereby incorporated by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be.

In one embodiment provided herein, antibodies, including but not limited to monoclonal and polyclonal antibodies, are raised against variant TNF-α proteins using methods known in the art. In a preferred embodiment, these anti-variant TNF-α antibodies are used for immunotherapy. Thus, methods of immunotherapy are provided. By "immunotherapy" is meant treatment of a TNF-α related disorders with an antibody raised against a variant TNF-α protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a variant TNF-α protein antigen to which antibodies are raised. As appreciated by one of ordinary skill in the art, the variant TNF-α protein antigen may be provided by injecting a variant TNF-α polypeptide against which antibodies are desired to be raised into a recipient, or contacting the recipient with a variant TNF-α protein encoding nucleic acid, capable of expressing the variant TNF-α protein antigen, under conditions for expression of the variant TNF-α protein antigen.

In a preferred embodiment, variant TNF-α proteins are administered as therapeutic agents, and can be formulated as outlined above. Similarly, variant TNF-α genes (including both the full-length sequence, partial sequences, or regulatory sequences of the variant TNF-α coding regions) may be administered in gene therapy applications, as is known in the art. These variant TNF-α genes can include antisense applications, either as gene therapy (i.e. for incorporation into the genome) or as antisense compositions, as will be appreciated by those in the art.

In a preferred embodiment, the nucleic acid encoding the variant TNF-α proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. U.S.A.* 83:4143-4146 (1986), incorporated by reference). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11:205-210 (1993), incorporated by reference). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. U.S.A.* 87:3410-3414 (1990), both incorporated by reference. For review of gene marking and gene therapy protocols see Anderson et al., *Science* 256:808-813 (1992), incorporated by reference.

In a preferred embodiment, variant TNF-α genes are administered as DNA vaccines, either single genes or combinations of variant TNF-α genes. Naked DNA vaccines are generally known in the art. Brower, *Nature Biotechnology,* 16:1304-1305 (1998). Methods for the use of genes as DNA vaccines are well known to one of ordinary skill in the art, and include placing a variant TNF-α gene or portion of a variant TNF-α gene under the control of a promoter for expression in a patient in need of treatment. The variant TNF-α gene used for DNA vaccines can encode full-length variant TNF-α proteins, but more preferably encodes portions of the variant TNF-α proteins including peptides derived from the variant TNF-α protein. In a preferred embodiment a patient is immunized with a DNA vaccine comprising a plurality of nucleotide sequences derived from a variant TNF-α gene. Similarly, it is possible to immunize a patient with a plurality of variant TNF-α genes or portions thereof as defined herein. Without being bound by theory, expression of the polypeptide encoded by the DNA vaccine, cytotoxic T-cells, helper T-cells and antibodies are induced which recognize and destroy or eliminate cells expressing TNF-α proteins.

In a preferred embodiment, the DNA vaccines include a gene encoding an adjuvant molecule with the DNA vaccine. Such adjuvant molecules include cytokines that increase the immunogenic response to the variant TNF-α polypeptide encoded by the DNA vaccine. Additional or alternative adjuvants are known to those of ordinary skill in the art and find use in the invention.

Pharmaceutical compositions are contemplated wherein a TNF-α variant of the present invention and one or more therapeutically active agents are formulated. Formulations of the present invention are prepared for storage by mixing TNF-α variant having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Lyophilization is well known in the art, see, e.g., U.S. Pat. No. 5,215,743, incorporated entirely by reference. Acceptable carriers, excipients, or stabilizers are nontoxic to recipients at the dosages and concentrations employed, and include buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches;

binding agents; additives; coloring agents; salt-forming counter-ions such as sodium; metal complexes (e.g. Zn-protein complexes); and/or non-ionic surfactants such as TWEEN®., PLURONICS® or polyethylene glycol (PEG). In a preferred embodiment, the pharmaceutical composition that comprises the TNF-α variant of the present invention may be in a water-soluble form. The TNF-α variant may be present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

Controlled Release

In addition, any of a number of delivery systems are known in the art and may be used to administer TNF-α variants of the present invention. Examples include, but are not limited to, encapsulation in liposomes, microparticles, microspheres (e.g. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-glutamate, ethylene-vinyl acetate, lactic acid-glycolic acid copolymers such as the LUPRON DEPOT®, and poly-D-(−)-3-hydroxyburyric acid. It is also possible to administer a nucleic acid encoding the TNF-α of the current invention, for example by retroviral infection, direct injection, or coating with lipids, cell surface receptors, or other transfection agents. In all cases, controlled release systems may be used to release the TNF-α at or close to the desired location of action.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, incorporated entirely by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be. The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, incorporated entirely by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be.

Dosage forms for the topical or transdermal administration of a DN-TNF-protein disclosed herein include powders, sprays, ointments, pastes, creams, lotions, gels, solutions, patches and inhalants. The DN-TNF-protein may be mixed under sterile conditions with a pharmaceutically-acceptable carrier, and with any preservatives, buffers, or propellants which may be required.

The ointments, pastes, creams and gels may contain, in addition to the DN-TNF-protein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the DN-TNF-protein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The administration of the variant TNF-α proteins of the present invention, preferably in the form of a sterile aqueous solution, may be done in any number of ways but is preferably administered centrally, directly into the spinal cord. In another embodiments administration may be done peripherally, i.e., not intracranially, in a variety of ways including, but not limited to, orally, subcutaneously, intravenously, intranasally, transdermally, intraperitoneally, intramuscularly, intrapulmonary, vaginally, rectally, or intraocularly. In some instances, intracranially may be preferred. In some instances, for example, in the treatment of wounds, inflammation, etc., the variant TNF-α protein may be directly applied as a solution, salve, cream or spray. The TNF-α molecules of the present may also be delivered by bacterial or fungal expression into the human system (e.g., WO 04046346 A2, hereby incorporated by reference).

In a preferred embodiment, variant TNF-α proteins are administered as therapeutic agents, and can be formulated as outlined above. Similarly, variant TNF-α genes (including both the full-length sequence, partial sequences, or regulatory sequences of the variant TNF-α coding regions) may be administered in gene therapy applications, as is known in the art. These variant TNF-α genes can include antisense applications, either as gene therapy (i.e. for incorporation into the genome) or as antisense compositions, as will be appreciated by those in the art.

In a preferred embodiment, the nucleic acid encoding the variant TNF-α proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. U.S.A. 83:4143-4146 (1986), incorporated entirely by reference). The oligonucleotides can be modified to enhance their uptake, e.g. by substituting their negatively charged phosphodiester groups by uncharged groups.

Dosage

Dosage may be determined depending on the disorder treated and mechanism of delivery. Typically, an effective amount of the compositions of the present invention, sufficient for achieving a therapeutic or prophylactic effect, ranges from about 0.000001 mg per kilogram body weight per day to about 10,000 mg per kilogram body weight per day. Suitably, the dosage ranges are from about 0.0001 mg per kilogram body weight per day to about 2000 mg per kilogram body weight per day. An exemplary treatment regime entails administration once every day or once a week or once a month. A DN-TNF protein may be administered on multiple occasions. Intervals between single dosages can be daily, weekly, monthly or yearly. Alternatively, A DN-TNF protein may be administered as a sustained release formulation, in which case less frequent administration is required. Dosage and frequency vary depending on the half-life of the agent in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity. Suitably, an effective amount (e.g., dose) of a DN-TNF protein described herein will provide therapeutic benefit without causing substantial toxicity to the subject. Toxicity of the agent described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agent described herein lies suitably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: The Pharmacological Basis of Therapeutics, Ch. 1 (1975).

EXAMPLES

Example 1: Toll-Like Receptor 4 Mediates Morphine-Induced Neuroinflammation and Tolerance Via Soluble Tumor Necrosis Factor Signaling Chronic opioid administration in rats induces a robust neuroinflammatory response via toll-like receptor 4 (TLR4) signaling in the periaqueductal gray (PAG), a key site for opioid-mediated analgesia, that drives tolerance (Wang X, et al. (2012) Proc Natl Acad Sci USA 109:6325-6330; Eidson L N, et al. (2013) J Neurosci 33:15952-15963). However, the mechanism by which TLR4 signaling leads to opioid tolerance was unknown. Morphine-induced TLR4 signaling increases proinflammatory cytokine production in the central nervous system (CNS) (Raghavendra V, et al. (2002) J Neurosci 22:9980-9989; Shen C H, et al. (2011) Anesth Analg 112:454-459) including tumor necrosis factor (TNF). TNF drives the release of itself and other proinflammatory cytokines (e.g., IL-1β, and IL-6) (Shen C H, et al. (2011) Anesth Analg 112:454-459; Shen C H, et al. (2011) Anesth Analg 113:184-190; Sun J, et al. (2012) Gene Ther 19:101-108), and robustly alters glutamate homeostasis and excitatory signaling in the CNS (Stellwagen D, et al. (2005) J Neurosci 25:3219-3228). Interestingly, many proposed mechanisms of opioid tolerance and dependence include a role for increased glutamatergic and/or decreased GABAergic signaling (Vaughan C W, et al. (1997) Nature 390:611-614; Bachtell R, et al. (2015) CNS Neurol Disord Drug Targets 14:692-699) that ultimately oppose the hyperpolarizing effects of morphine. TNF naturally exists in two forms; the more common form, transmembrane TNF (tmTNF), and the less abundant form, soluble TNF (solTNF) (Kriegler M, et al. (1988) Cell 53:45-53). Although spinal TNF has been implicated in opioid tolerance maintenance (Shen C H, et al. (2011) Anesth Analg 112:454-459), TNF has not been examined in isolation in the development of opioid tolerance, and it is not known which form of TNF mediates tolerance development and glutamatergic signaling.

This Example tests the hypothesis that TLR4 elicits opioid tolerance via solTNF-mediated increases in PAG immune signaling and disruption of glutamate reuptake. To test this hypothesis, PAG solTNF was manipulated using a lentivirus encoding dominant negative TNF or XPro1595, a PEGylated brain-permeant peptide, to sequester solTNF and examined the impact on tolerance, cytokine expression, and key elements of glutamate homeostasis. Results demonstrate for the first time that the soluble form of TNF (and not transmembrane TNF) increases cytokine expression and alters glutamate homeostasis within the PAG, identifying a mechanism driving the development of opioid tolerance. Together, these results suggest a pharmacological target to enhance the efficacy of opioid analgesia in the clinic while minimizing the risk of dependence and addiction.

Materials and Methods

Subjects

Male Sprague Dawley rats (250-350 g; Charles River; MA) were pair-housed on a 12:12 hour light:dark cycle (lights on at 7:00 am) with ad libitum access to food and water. The Institutional Animal Care and Use Committee at Georgia State University approved all studies.

Lentiviral Dominant Negative TNF

The human full-length DN-TNF DNA sequence (TNF variant with two point mutations; A145R/197T (Steed P M, et al. (2003) Science 301:1895-1898)) and the enhanced green fluorescent protein DNA sequence (GFP; reporter)

were subcloned into a lentiviral vector under the control of the chicken β-actin cytomegalovirus (CAG) promoter as previously published (McCoy M K, et al. (2008) Mol Ther 16:1572-1579).

Lentivirus Infection and Morphine Treatment

Bilateral intra ventrolateral PAG (vlPAG) infusion of lenti-DN-TNF or lenti-GFP were performed. One week later, morphine (5 mg/kg, sc; National Institute on Drug Abuse, Bethesda, Md.) or vehicle (saline; 1 ml/kg; sc) was administered once a day for 3 consecutive days, resulting in four groups: lenti-DN-TNF+Morphine (n=10), lenti-DNTNF+Saline (n=5), lenti-GFP+Morphine (n=10), and lenti-GFP+Saline (n=4).

Cannulation, Lentivirus Infection, and LPS Microinfusions

Rats were implanted with bilateral cannula aimed at the ventrolateral PAG (vlPAG) and received bilateral infusions of lenti-DN-TNF or lenti-GFP while under surgical anesthesia. One week following viral vector infusion, cannulated rats received daily bilateral intra-vlPAG lipopolysaccharide or saline for three days to induce a naïve morphine tolerance resulting in the following groups: lenti-DN-TNF+PAG LPS (n=9), lenti-DN6 TNF+PAG Saline (n=6), lenti-GFP+PAG LPS (n=4), and lenti-GFP+PAG Saline (n=6).

XPro1595 and Morphine Treatment

XPro®1595 (10 mg/kg; sc), a brain permeant TNF variant that selectively inhibits soluble TNF signaling (>2500-fold) (Steed P M, et al. (2003) Science 301:1895-1898; Zalevsky J, et al. (2007) J Immunol 179:1872-1883), or saline was administered 1 day before the first morphine (5 mg/kg; sc) injection and with the final (3rd) morphine injection (half life=18 hours), resulting in the following groups: XPro+Morphine (n=11), XPro+Saline (n=8), Vehicle+Morphine (n=11), and Vehicle+Saline (n=8).

Behavioral Testing

Nociception (paw withdrawal latency) was assessed using the paw thermal stimulator (Hargreaves K, et al. (1988) Pain 32:77-88).

In situ hybridization analysis of GLAST, GLT-1 and the neuronal excitatory amino acid carrier 1 (EAAC1).

In a subset of rats (n=4-6/group), in situ hybridization for GLAST, GLT-1 and the neuronal excitatory amino acid carrier 1 (EAAC1) mRNA was performed using 35S-UTP-labeled RNA probes generated from cloned fragments of cDNA derived from rat brain tissue as described previously (Inoue et al., 2004). Changes in mRNA were assessed using ANOVA, and Fisher's post hoc tests when a significant main effect was observed (SPSS). Mean specific hybridization is reported as the disintegrations per minute per milligram of tissue (dpm/mg)+SEM; $p<0.05$ was considered significant.

XPro1595 Measurement

Immediately following tolerance assessment, cerebrospinal fluid (CSF) was collected via cisterna magna, and plasma and brains were collected (in under 2 minutes). Midbrain, CSF, and plasma XPro1595 was quantified.

qPCR analysis of proinflammatory cytokines and TLR4 mRNA Brains were collected from rats (n=5/group treated with XPro+Morphine, XPro+Saline, Vehicle+Morphine, and Vehicle+Saline, blocked (Bregma −6.96 to −8.52), and 1 mm bilateral micropunches were taken through the vlPAG for quantitative RT-PCR of proinflammatory cytokines and TLR4 mRNA.

Gene expression is reported as the ratio of the gene of interest to Gapdh, and are normalized to the Vehicle+Saline condition. Changes in mRNA between groups were assessed using an ANOVA on ranks (Kruskal-Wallis), and Mann Whitney U post-hoc comparisons (SPSS). Data are expressed as median; $p<0.05$ was considered significant.

Results

Sequestration of Ventrolateral PAG Soluble TNF Eliminated Tolerance to Systemic Morphine The initial series of experiments determined if sequestration of soluble TNF (solTNF) attenuated the development of tolerance to systemic morphine. The DN-TNF rapidly forms heterotrimers with native soluble TNF (solTNF), effectively sequestering endogenous solTNF and inhibiting TNFRI binding (Steed P M, et al. (2003) Science 301:1895-1898), while sparing transmembrane TNF (tmTNF) signaling (Steed et al., 2003, Zalevsky et al., 2007). Human DN-TNF and green fluorescent protein (GFP) or GFP alone was bilaterally expressed in the ventrolateral PAG (vlPAG) of adult male rats via lenti-viral infection 7 days prior to systemic morphine (5 mg/kg; $ED_{50}$ dose (Loyd D R, et al. (2008) Eur J Neurosci 27:1517-1)) or saline (1 ml/kg), once daily for 3 consecutive days to induce tolerance.

Figure 1B:
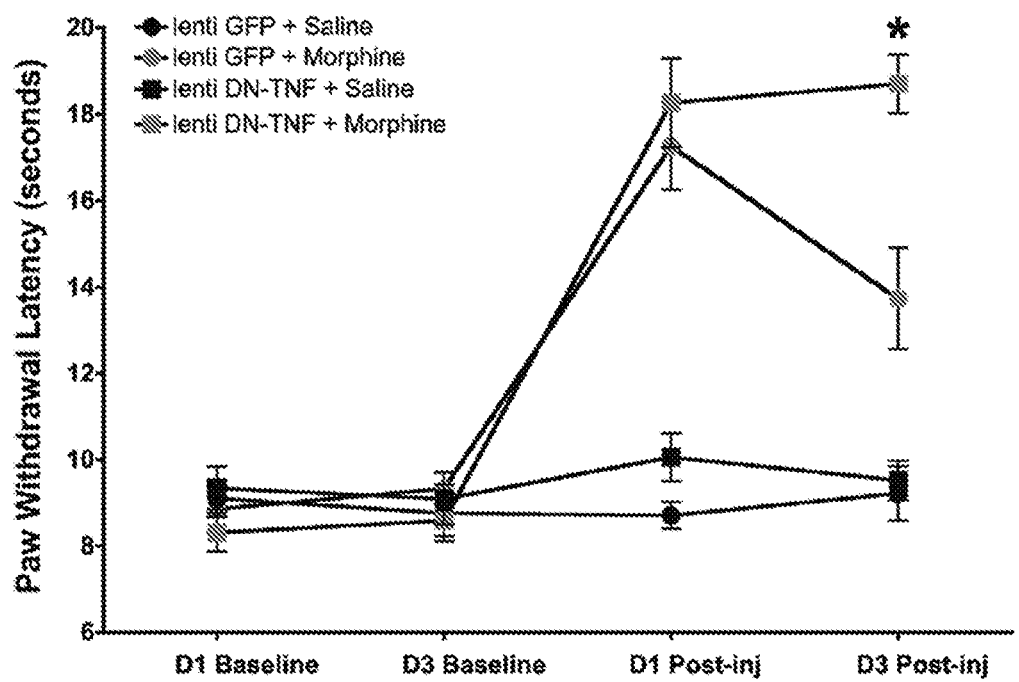
Figure 1C:
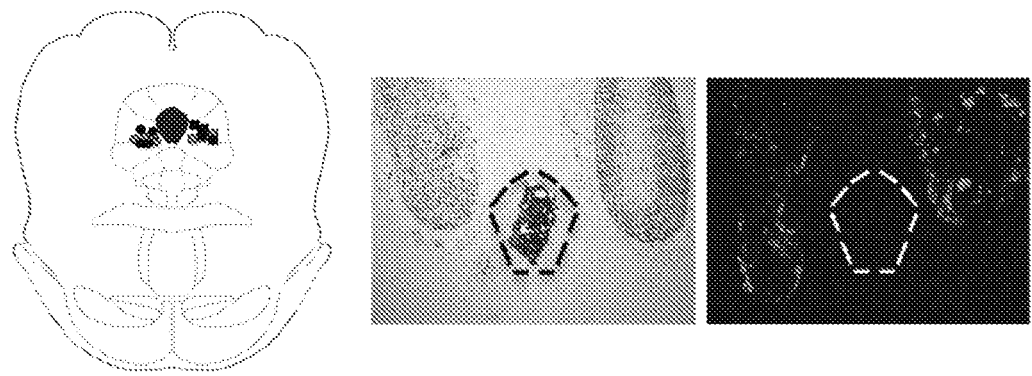

Robust virus-induced GFP expression (FIG. 1A) was observed bilaterally in the vlPAG as indicated by Fluorescein isothiocyanate (FITC) microscopy (FIG. 1C). Baseline and postinjection paw withdrawal latencies did not differ between lenti-DN-TNF and lenti-GFP rats treated with systemic saline, indicating that DN-TNF expression did not alter basal nociceptive thresholds (FIG. 1B). Administration of morphine on Day 1 and Day 3 produced an increase in both lenti-DN-TNF treated rats and lenti-GFP controls. Two way ANOVA revealed a significant interaction between solTNF sequestration and morphine efficacy across time, $F_{(9, 54)}=23.51$; $p<0.0001$. Morphine efficacy did not differ between lenti-DN-TNF+Morphine and lenti-GFP+Morphine groups on Day 1 (1st morphine injection; $p>0.05$). On Day 3, morphine was significantly more efficacious in lenti-DN-TNF+Morphine treated rats than lenti-GFP+Morphine treated rats (3rd morphine injection; $p<0.0001$) indicative of tolerance only in the lenti-GFP+Morphine group.

Figure 1D:
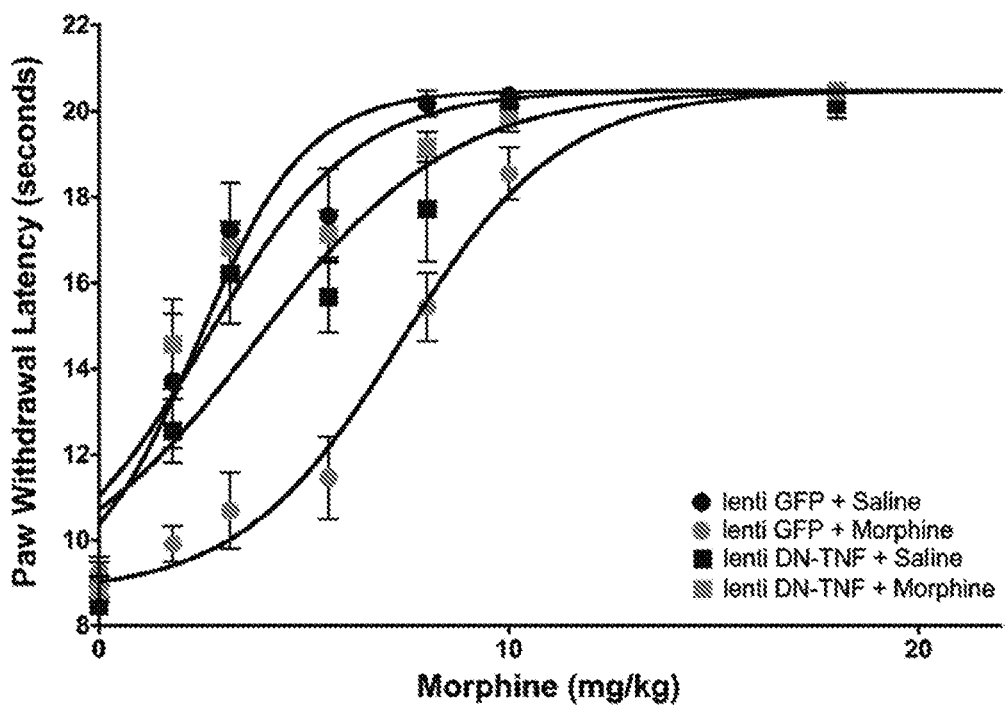

Administration of cumulative doses of morphine on Day 4 produced an increase in paw withdrawal latency in all rats tested (FIG. 1D; $F_{(3, 195)}=49.64$, $p<0.0001$). Post hoc analysis revealed that lenti-GFP+Morphine treated rats were tolerant to morphine, as indicated by a threefold rightward shift in the dose-response curve ($ED_{50}=7.47$ mg/kg, as compared with lenti-GFP+Saline controls, $ED_{5}(\ )=2.50$ mg/kg; $p=0.01$; Table 2). Intra-vlPAG pretreatment with lenti-DN-TNF preserved the antinociceptive potency of morphine ($ED_{50}=2.66$ mg/kg) compared with rats made tolerant to morphine (lenti-DN-TNF+Morphine vs. lenti9 GFP+Morphine; $p=0.01$). Indeed, lenti-DN-TNF+Morphine-treated rats did not differ from rats who received saline prior to the morphine challenge ($p=0.15$).

TABLE 2

Summary of morphine $ED_{50}$s following chronic morphine administration

| Condition | n | $ED_{50}$ (mg/kg) | 95% Confidence Interval |
|---|---|---|---|
| lenti GFP + Saline | 4 | 2.50 | 1.86-3.06 |
| lenti GFP + Morphhine | 10 | 7.47 | 6.90-8.03 |
| lenti DN-TNF + Saline | 5 | 3.93 | 2.97-4.88 |
| lenti DN-TNF + Morphine | 10 | 2.66 | 2.14-3.18 |
| $F_{(3,195)} = 49.64$; p < 0.0001 | | | |
| lenti GFP + PAG Saline | 6 | 2.37 | 2.05-2.70 |
| lenti GFP + PAG LPS | 4 | 6.00 | 5.42-6.58 |
| lenti DN-TNF + PAG Saline | 6 | 3.00 | 2.61-3.40 |
| lenti DN-TNF + PAG LPS | 9 | 3.26 | 2.90-3.62 |
| $F_{(3,167)} = 37.31$; p < 0.0001 | | | |

TABLE 2-continued

Summary of morphine $ED_{50}$s following chronic morphine administration

| Condition | n | $ED_{50}$ (mg/kg) | 95% Confidence Interval |
|---|---|---|---|
| Vehicle + Saline | 8 | 2.30 | 1.99-2.60 |
| Vehicle + Morphine | 11 | 7.35 | 6.82-7.88 |
| XPro + Saline | 8 | 3.18 | 2.69-3.67 |
| XPro + Morphine | 11 | 2.25 | 1.86-2.65 |

$F_{(3,258)} = 87.31; p < 0.0001$

Figure 1E:
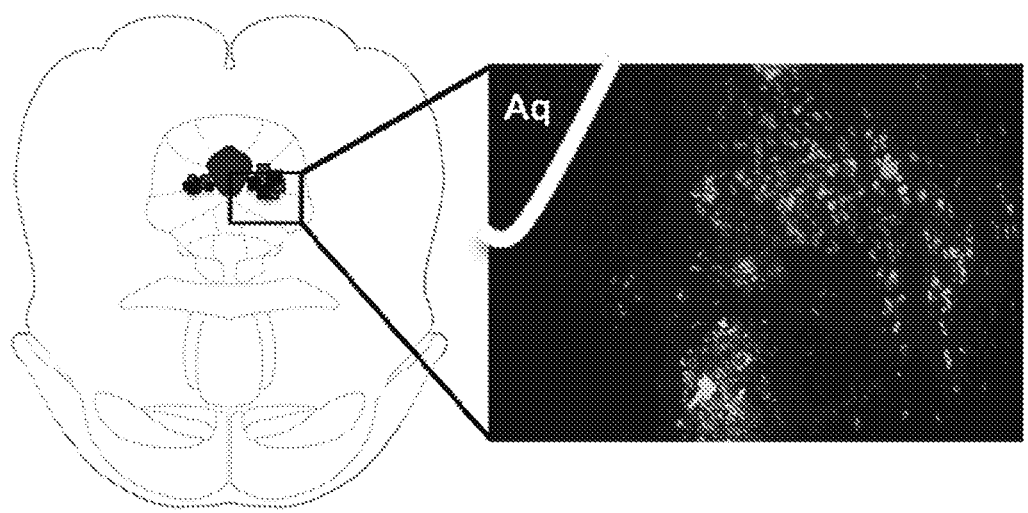
Figure 1F:
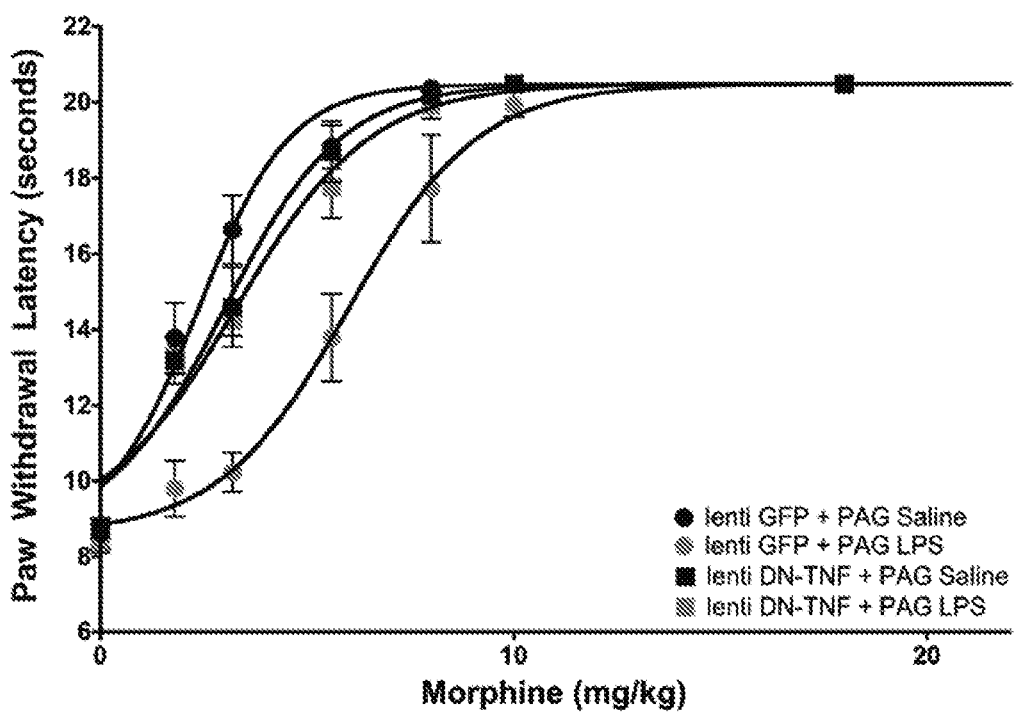

Sequestration of vlPAG soluble TNF eliminated morphine tolerance induced by vlPAG LPS To test the hypothesis that morphine acts through TLR4 to increase solTNF signaling and decrease morphine efficacy, the above experiment were repeated in rats that received intravlPAG infusions of the prototypical TLR4 agonist LPS for three days to induce a naïve tolerance to morphine. Robust virus-induced GFP expression was observed bilaterally in the vlPAG (FIG. 1E). Intra-PAG administration of LPS had no effect on baseline paw withdrawal latencies when measured 24 and 72 hours later. Administration of cumulative doses of morphine on Day 4 (first morphine exposure) produced an increase in paw withdrawal latency in all rats tested (FIG. 1F; significant main effect of treatment: $F(3,167)=37.31$, $p<0.001$). Three intra-vlPAG infusions of LPS was sufficient to induce 'naïve' tolerance to morphine, as indicated by a rightward shift in the morphine dose response curve (lenti-GFP+PAG LPS, $ED_{50}=6.00$ mg/kg) as compared with lenti-GFP+PAG Saline controls ($ED_{50}=2.37$ mg/kg; $p=0.02$). IntravlPAG pretreatment with lenti-DN-TNF preserved the antinociceptive potency of morphine (lenti-DN-TNF+PAG LPS, $ED_{50}=3.26$ mg/kg) compared with rats made tolerant to morphine by vlPAG LPS (lenti-GFP+PAG LPS; $p=0.01$). Indeed, lenti-DN-TNF+PAG LPS rats did not differ from lenti-DN-TNF+PAG Saline controls ($p=0.07$). These results demonstrate that LPS mimics the effects of morphine, acting through TLR4 to increase solTNF signaling and decrease morphine efficacy (i.e., induce tolerance).

Figure 2A:
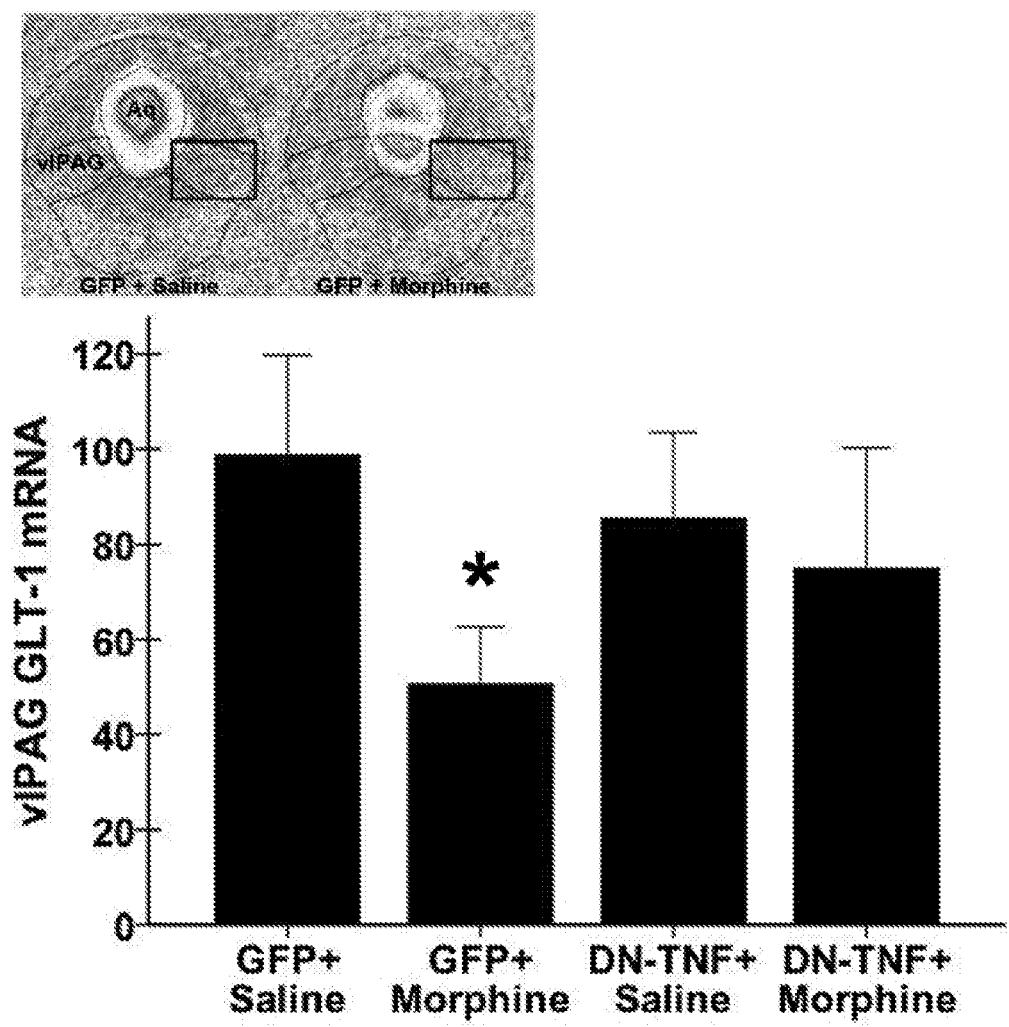
FIGS. 2A to 2F show viral vector-mediated sequestration of soluble TNF in the vlPAG attenuates the systemic morphine-induced and vlPAG LPS-induced decrease in astrocytic glutamate transporter mRNA in the vlPAG.
Figure 2B:
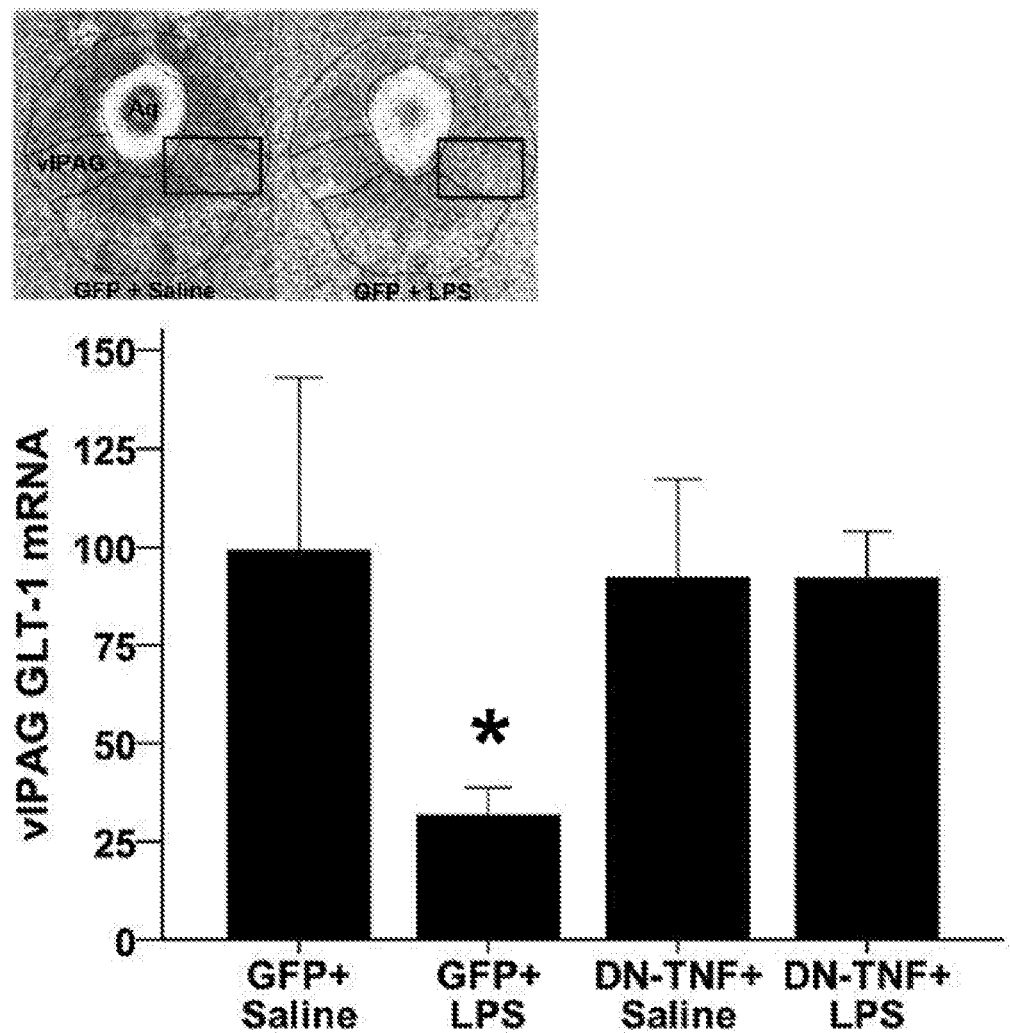
Figure 2C:
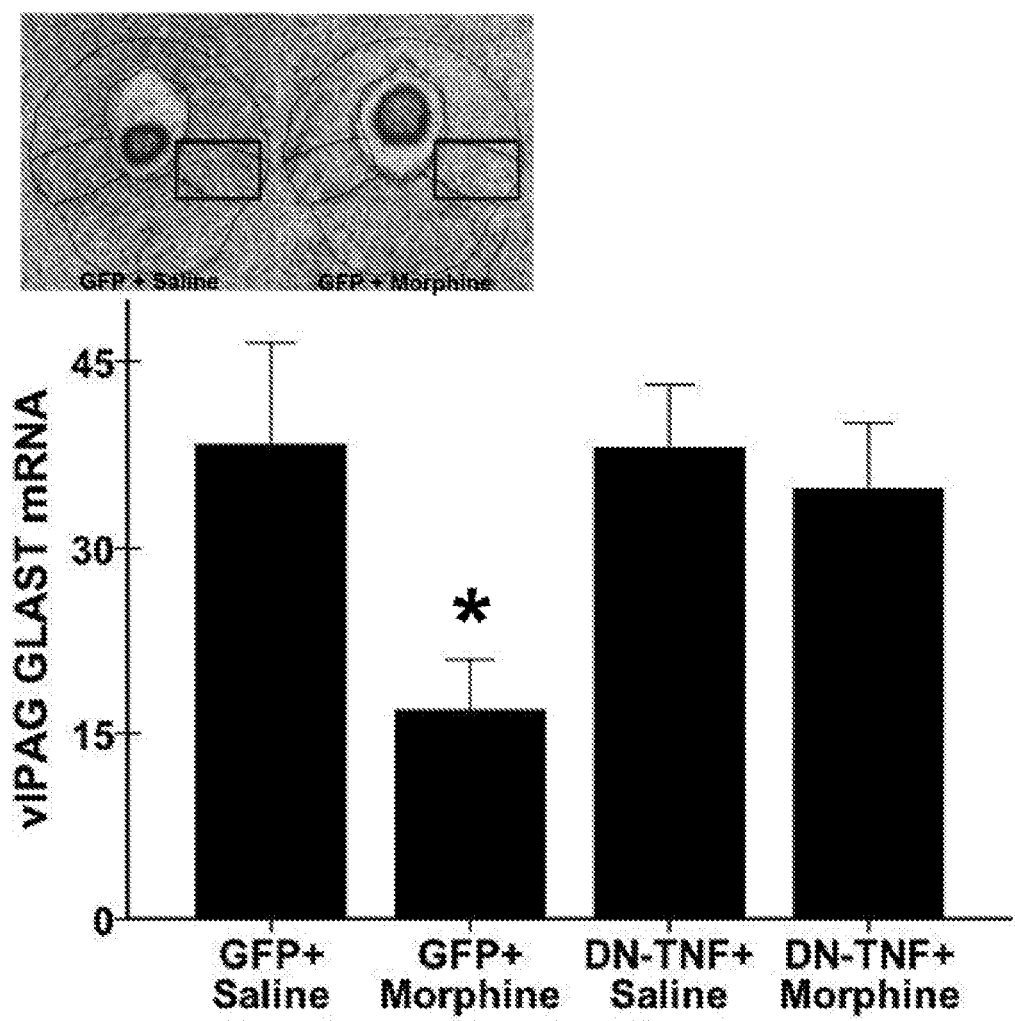
Figure 2D:
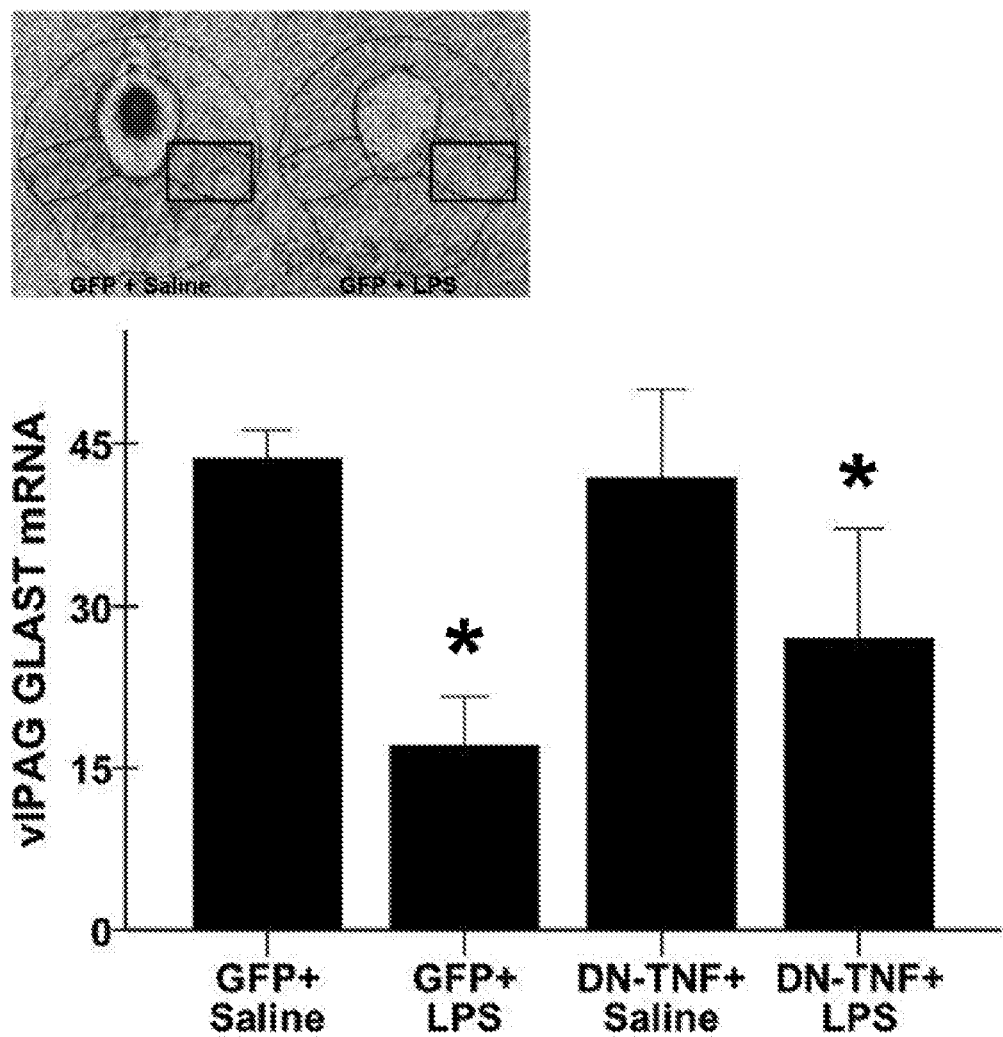
Figure 2E:
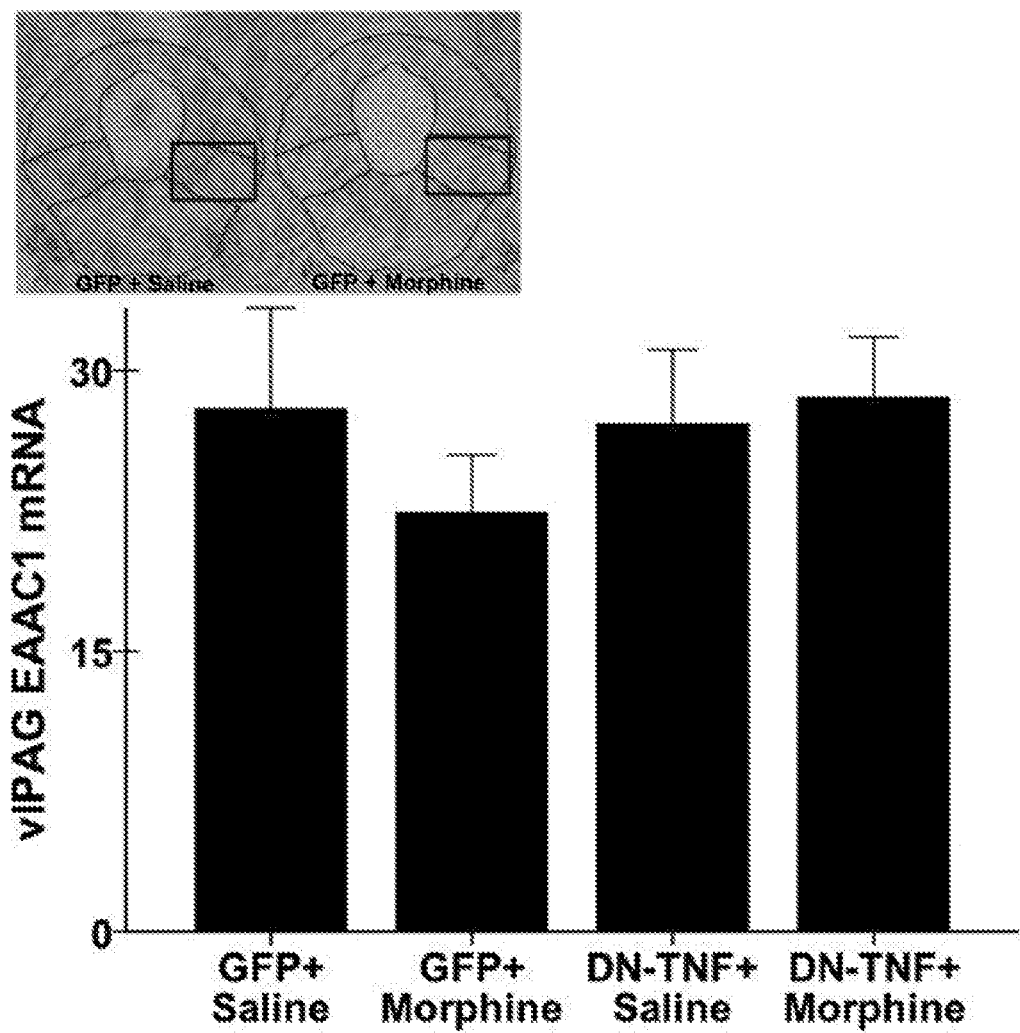
Figure 2F:
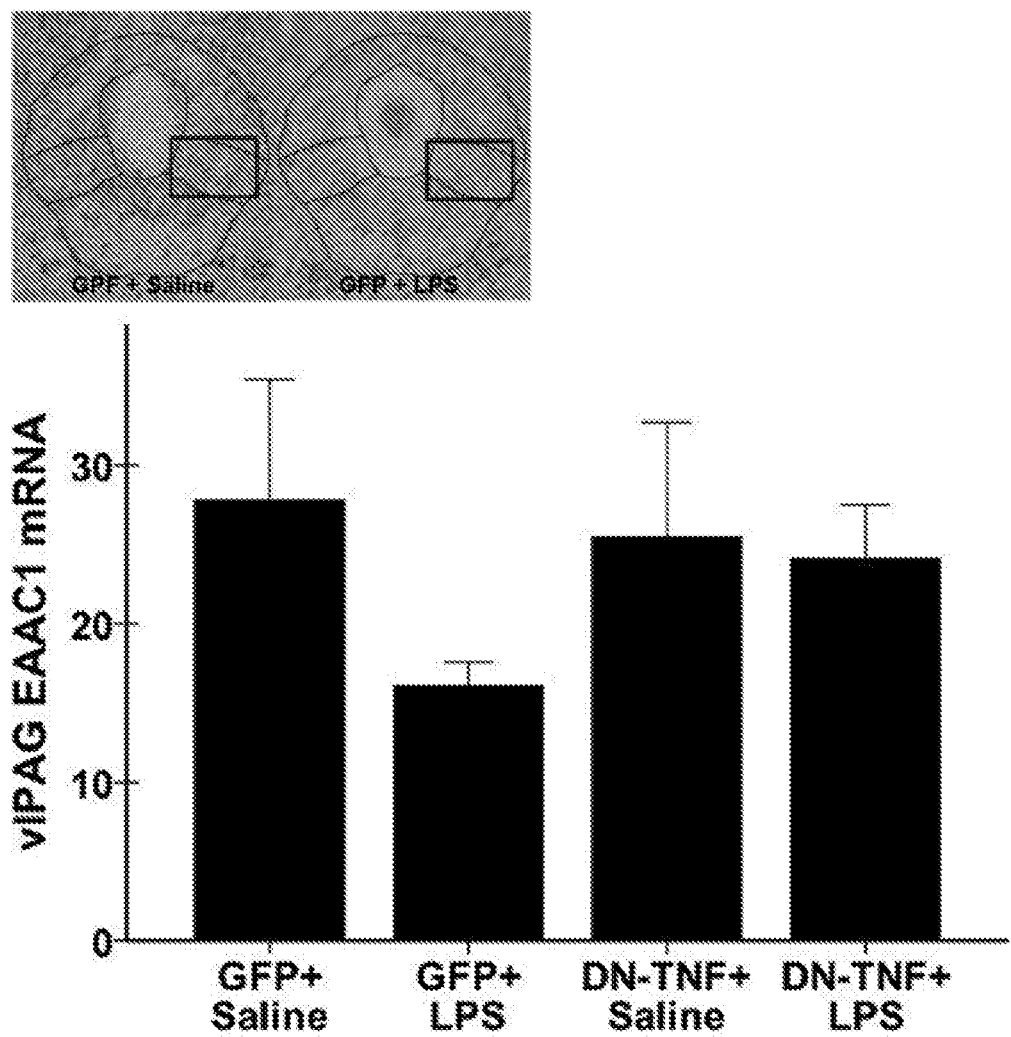

Chronic Systemic Morphine Decreased vlPAG GLT-1 and GLAST mRNA in a solTNF-Dependent Manner Next tested was the hypothesis that solTNF contributes to tolerance development by decreasing astrocytic GLT-1 and GLAST, the primary source of glutamate reuptake in the brain (60-80% (Rothstein J D, et al. (1996) Neuron 16:675-686)); changes in the neuronal glutamate transporter EAAC1 were also investigated. mRNA in the caudal vlPAG of rats treated with lenti-GFP+Morphine, lenti-DN-TNF+Morphine, lenti-GFP+Saline, and lenti-DN-TNF+Saline were determined using in situ hybridization. Morphine administration for 3 days significantly decreased vlPAG GLT-1 mRNA, as compared with saline controls (main effect of treatment: $F(3,23)=3.58$, $p=0.03$; lenti-GFP+Morphine vs. lenti-GFP+Saline; $p=0.004$; FIG. 2A). Lentiviral expression of DN-TNF in the vlPAG rescued the expression of GLT-1 mRNA, such that lenti-DN-TNF+Morphine rats did not differ from lenti-GFP+Saline controls ($p=0.13$). Similar to what was noted for GLT-1 mRNA, chronic morphine significantly decreased vlPAG GLAST mRNA as compared with saline controls (main effect of treatment: $F(3,26)=6.681$, $p=0.002$; lenti-GFP+Morphine vs. lenti-GFP+Saline; $p<0.001$; FIG. 2C). vlPAG DN-TNF expression prevented morphine-induced decrease in vlPAG GLAST mRNA, as lenti-DN-TNF+Morphine rats did not differ from lenti-GFP+Saline controls ($p=0.49$). No significant effect of treatment was noted in vlPAG EAAC1 mRNA expression ($F(3,26)=0.876$, $p=0.47$; FIG. 2E), suggesting that morphine preferentially alters astrocytic, and not neuronal, glutamate transport in the vlPAG.

Chronic vlPAG TLR4 Agonism Decreased vlPAG GLT-1 and GLAST mRNA in a solTNF-Dependent Manner Given that LPS binding to TLR4 is a potent inducer of TNF expression, it was hypothesized that GLT-1 and GLAST would be decreased in rats made tolerant to morphine by LPS (naïve tolerance). Consistent with results from chronic systemic morphine exposure, chronic vlPAG microinfusions of LPS decreased vlPAG GLT-1 and GLAST mRNA ($F(3,12)=7.268$, $p=0.01$, and $F(3,10)=7.321$, $p=0.01$, respectively), and did not alter vlPAG EAAC1 mRNA ($F(3,10)=1.982$, $p=0.17$; FIG. 2B,D,F). Lenti-GFP+PAG LPS rats had significant decreases in GLT-1 and GLAST mRNA as compared with lenti-GFP+PAG Saline rats ($p=0.005$, FIG. 2B and $p=0.002$, FIG. 2d, respectively). vlPAG DN-TNF expression rescued GLT-1 mRNA (lenti-DN-TNF+PAG LPS vs. lenti-GFP+PAG Saline; $p=0.72$), and increased, but did not rescue GLAST mRNA (lenti-DN-TNF+PAG LPS vs. lenti-GFP+PAG Saline; $p=0.04$).

Figure 3A:
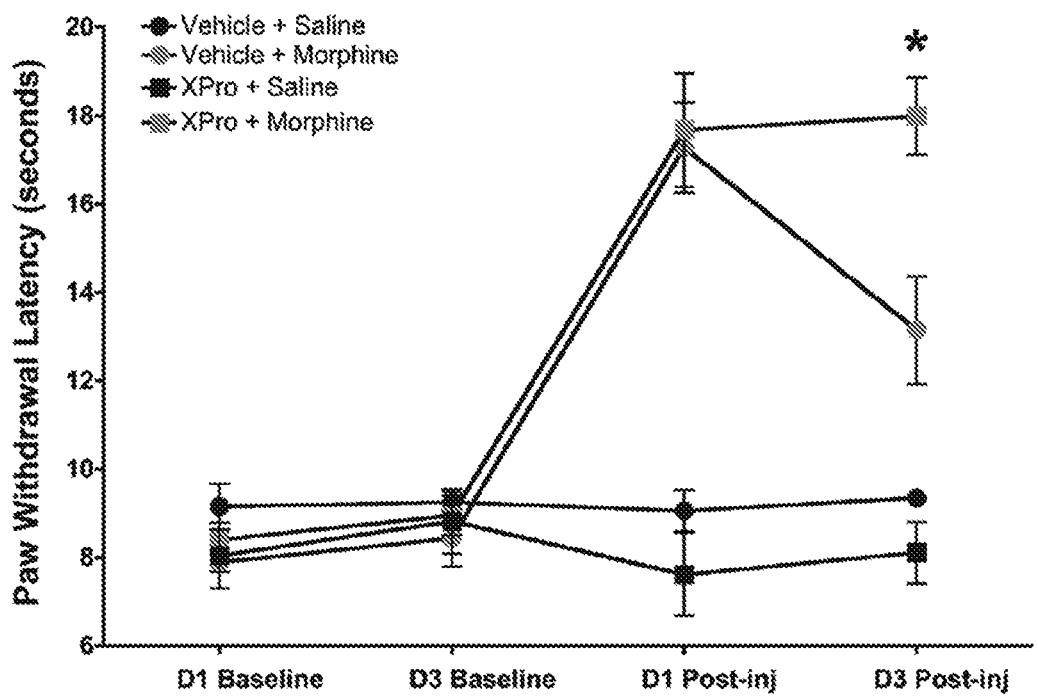
FIGS. 3A and 3B are a summary of acute morphine analgesia and morphine tolerance following systemic XPro1595 and morphine. Systemic administration of XPro1595 prevents the development of tolerance to morphine.

Systemic Administration of the Soluble TNF Inhibitor XPro1595 Prevented Morphine Tolerance Next tested was the effect of systemic XPro1595 on morphine tolerance using the same paradigm as above. XPro1595 (10 mg/kg; sc) or vehicle (saline; 1 ml/kg; sc) was administered 1 day prior to the first morphine/saline injection, and with the third morphine/saline injection. Two way ANOVA revealed a significant interaction between solTNF sequestration and morphine efficacy across time, $F(9, 42)=14.15$; $p<0.0001$ (FIG. 3A). Morphine efficacy did not differ between rats treated with XPro1595+Morphine and those treated with Vehicle+Morphine on Day 1 (1st morphine injection; $p>0.05$). On Day 3, morphine was significantly more efficacious in XPro1595+Morphine treated rats than Vehicle+Morphine treated rats ($p<0.001$).

Figure 3B:
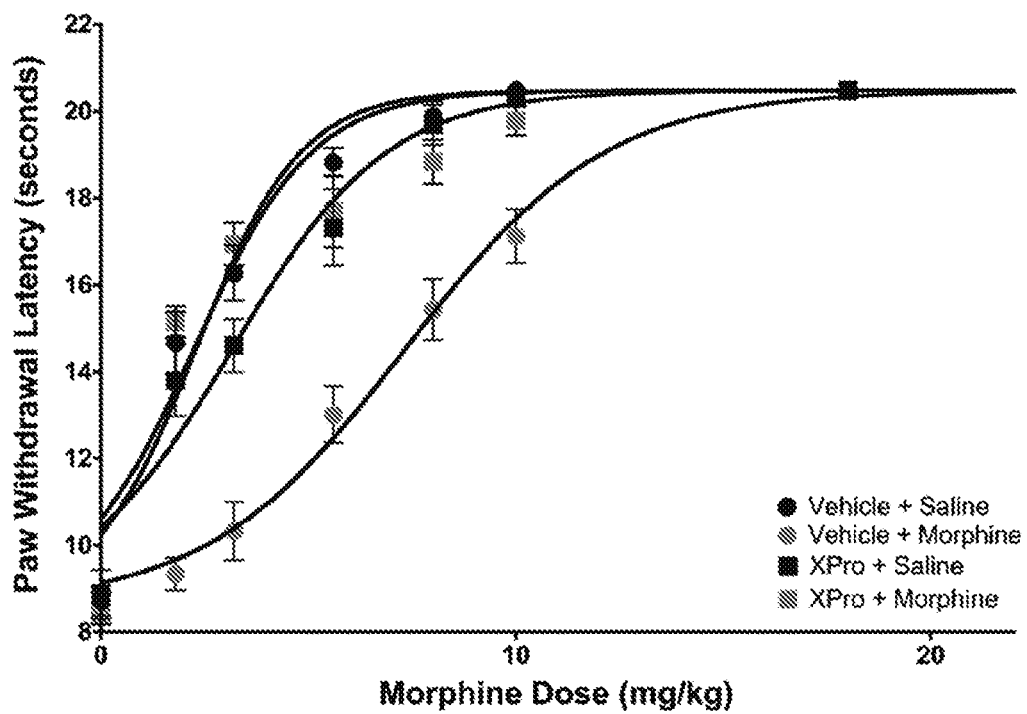

Administration of cumulative doses of morphine on Day 4 produced an increase in nociceptive thresholds in all rats tested (FIG. 3B; $F(3,258)=87.31$, $p<0.0001$). Vehicle+Morphine treated rats were tolerant to morphine ($ED_{50}=8.03$ mg/kg), in comparison to Vehicle+Saline rats ($ED_{50}=2.31$ mg/kg; $p<0.001$). Systemic pretreatment with XPro1595 preserved the antinociceptive potency of morphine (XPro+Morphine; $ED_5(\ )=3.08$ mg/kg) compared with vehicle-treated rats that were tolerant to morphine (Vehicle+Morphine; $p<0.001$). An ELISA for human TNF (hTNF) revealed robust XPro1595 levels in plasma, CSF, and midbrain tissue. Indeed, midbrain levels strongly correlated with CSF levels of hTNF ($R2=0.87$), indicating efficient transport into the brain. hTNF was not detected in Vehicle+Morphine or Vehicle+Saline treated rats.

Figure 4A:
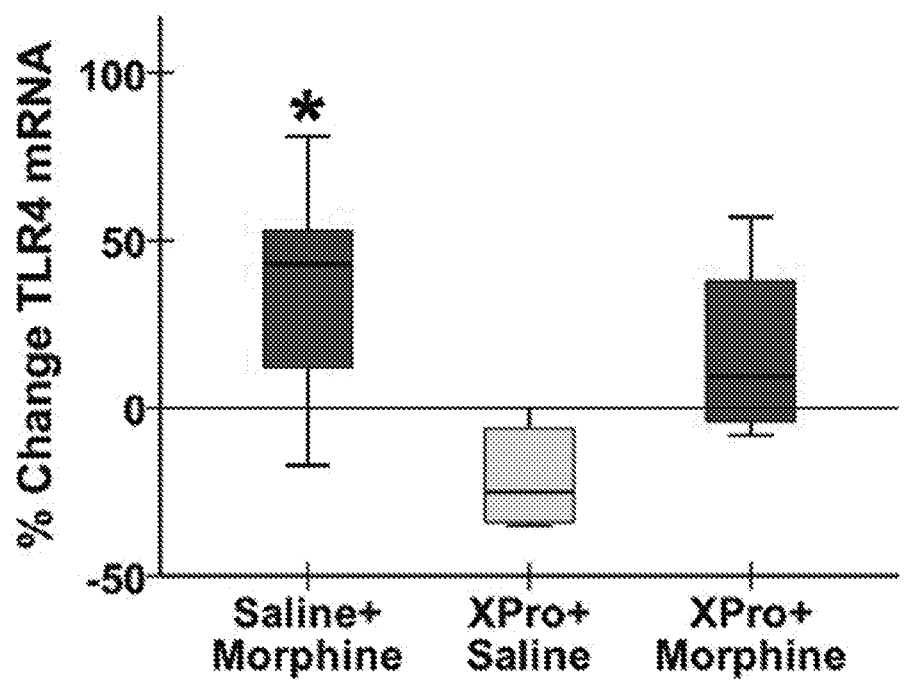
FIGS. 4A to 4F are a summary of cytokine and TLR4 mRNA in the vlPAG following chronic systemic XPro1595 and morphine. Systemic administration of XPro1595 prevents morphine induced increases in vlPAG IL-1β and TLR4 mRNA. Tlr4 (FIG. 4A), Il1β (FIG. 4B), Tnf (FIG. 4C), Il6 (FIG. 4D), and Il10 (FIG. 4E) mRNA levels relative to the housekeeping gene Gapdh in the vlPAG of rats treated with Saline+Morphine, XPro+Saline, and XPro+Morphine. Data are represented as median % change from Vehicle+Saline controls; n=5 per group.

Systemic Administration of XPro1595 Abolished Morphine-Induced Increases in vlPAG TLR4 and IL-1β mRNA TNF and TLR4 are major regulators of cytokine expression in the CNS (e.g., IL-6, IL-1β, and TNF), and cytokines, including IL-1β and IL-6, have been implicated in morphine tolerance. The hypothesis that chronic morphine increases proinflammatory cytokine expression in the vlPAG in a solTNF-dependent manner was tested. Changes in vlPAG TLR4 mRNA were also assayed. qPCR revealed that morphine significantly increased vlPAG TLR4 expression ($H=7.49$, 2 df, $p=0.02$, FIG. 4A), such that TLR4 gene expression significantly increased in Vehicle+Morphine treated rats as compared with XPro+Saline controls ($W=15$; $p=0.02$). Co-administration of XPro1595 with morphine normalized TLR4 mRNA as XPro+Morphine and XPro+

Figure 4B:
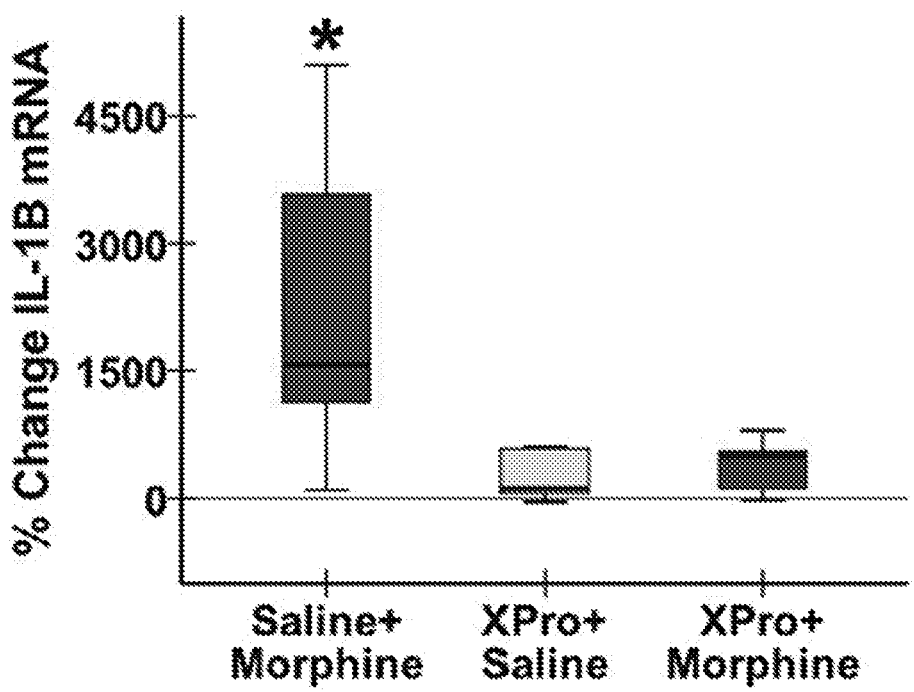
Figure 4C:
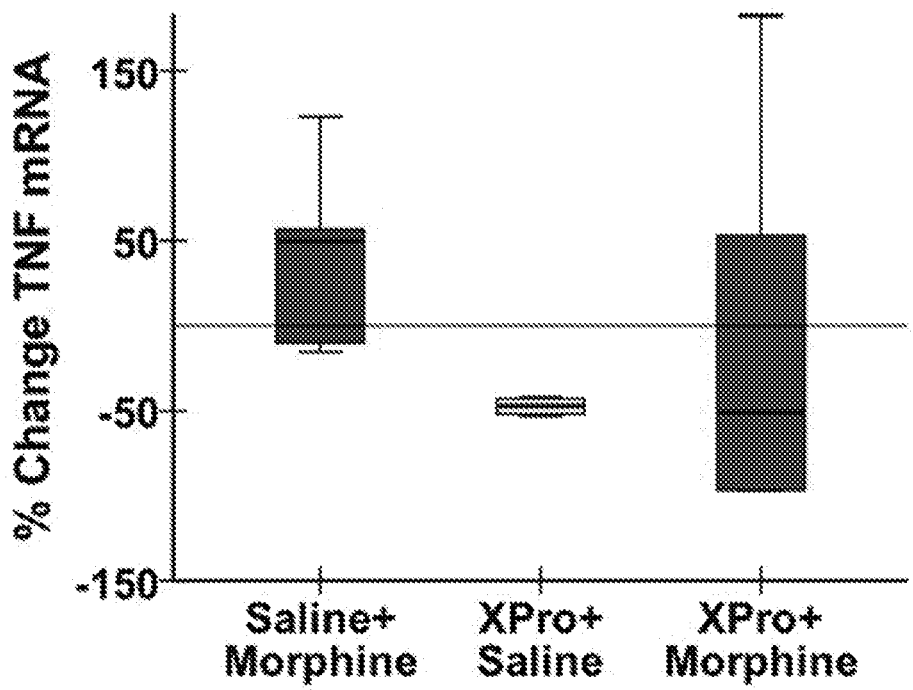
Figure 4D:
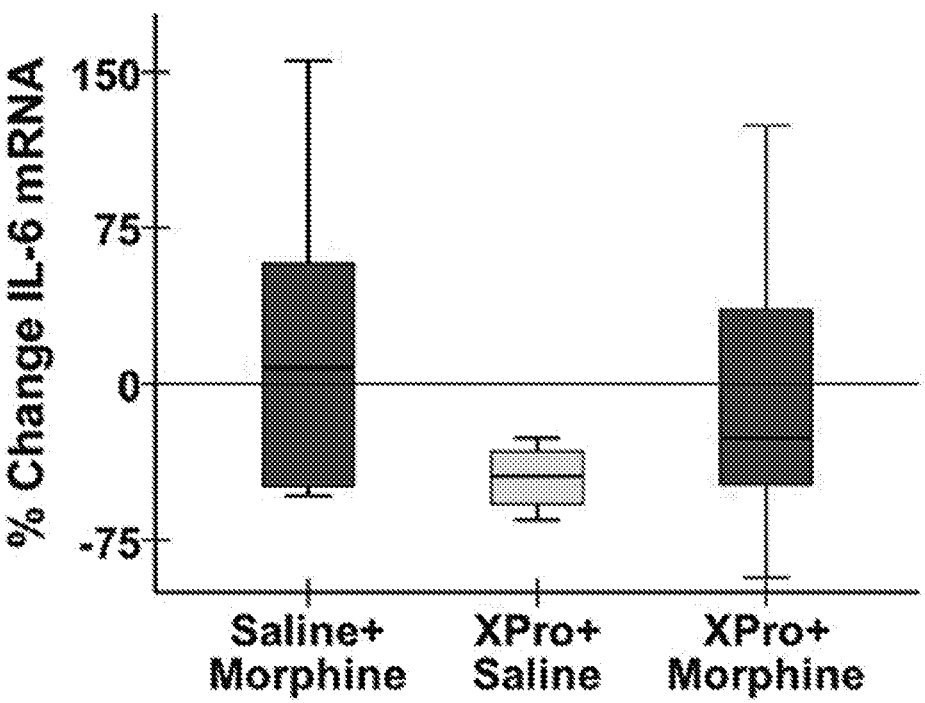
Figure 4E:
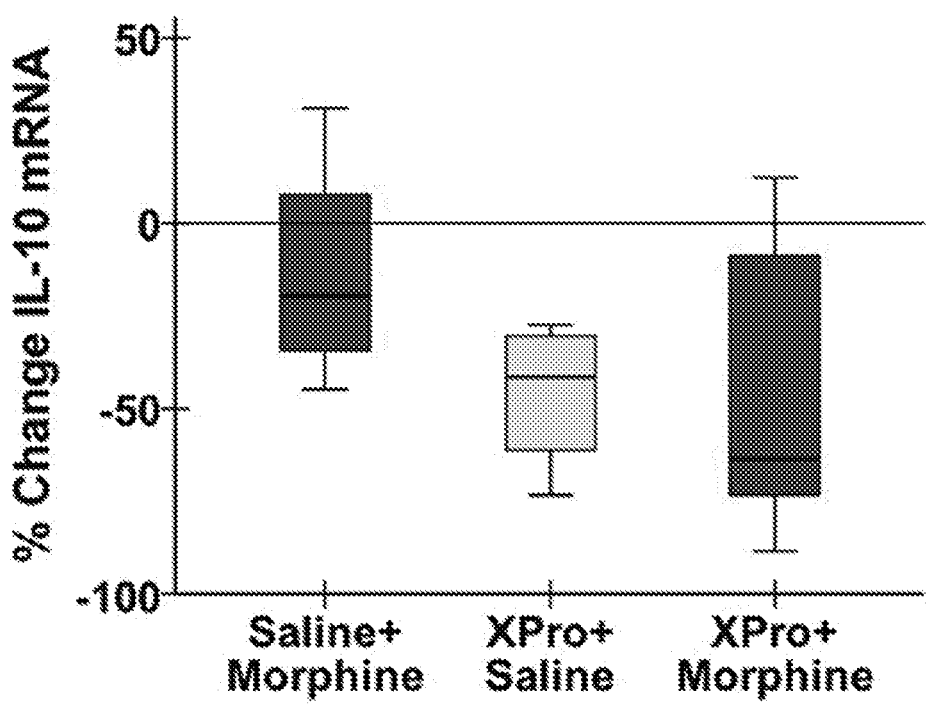
Figure 4F:
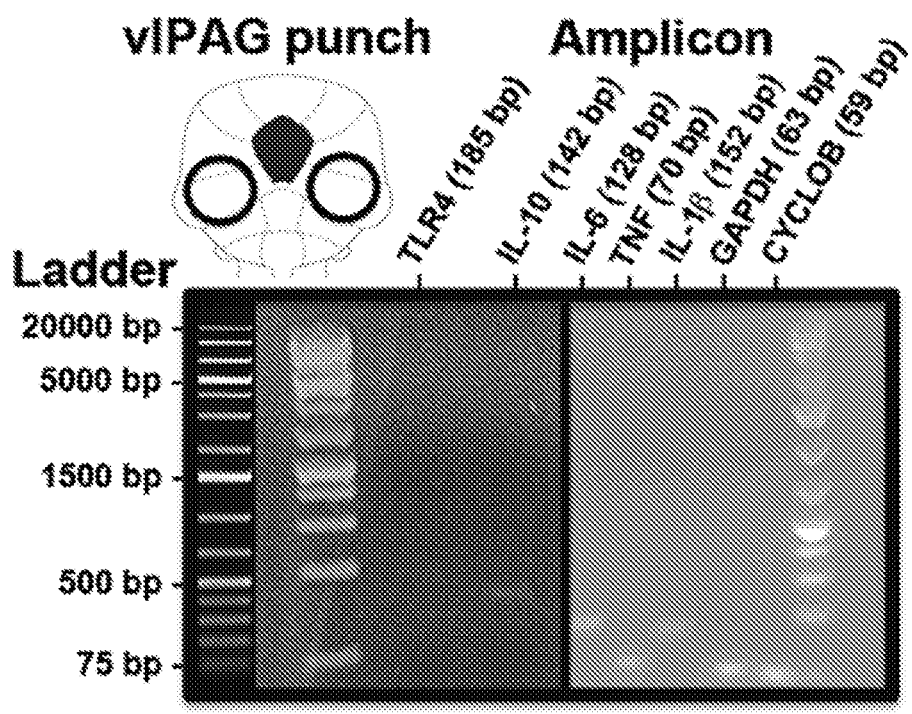

Saline rats did not differ (W=17.5, p=0.06). A significant main effect of treatment was also observed for vlPAG IL-1β mRNA by 3,500% (Kruskal-Wallis, H=8.05, 2 df, p=0.02, FIG. 4B) as compared with Vehicle+Saline controls, a nearly 30-fold increase. Co-administration of systemic XPro1595 and morphine eliminated the increase in IL-1β gene expression (W=26; p=0.84). The increase in TNF gene expression was not statistically significant (Kruskal-Wallis, H=4.00, 2 df, p=0.14). No significant change in IL-6 or IL-10 mRNA was noted.

Discussion

TLR4 signaling contributes to the adverse consequences of chronic opioid use Chronic morphine administration leads to the induction of a neuroinflammatory response (Eidson L N, et al. (2013) J Neurosci 33:15952-15963), resulting in a significant increase in glutamatergic tone and excitatory neurotransmission (Fine S M, et al. (1996) J Biol Chem 271:15303-15306; Ogoshi F, et al. (2005) Exp Neurol 193: 384-393) that together, actively oppose the analgesic effect of morphine (Trujillo K A, et al. (1991) Science 251:85-87; Wong C S, et al. (2002) Can J Anaesth 49:561-565). These same characteristics underlie opioid dependence, withdrawal, and addiction, implicating a common underlying mechanism (Hutchinson M R, et al. (2007) ScientificWorld-Journal 7:98-111). PAG TLR4 is necessary for the development of morphine tolerance, and there is a growing body of literature implicating TLR4 in opioid reward and reinforcement (Bachtell R, et al. (2015) CNS Neurol Disord Drug Targets 14:692-699). TLR4 binds opioids, including morphine, resulting in production of a milieu of proinflammatory signaling factors (e.g., TNF and IL-1β; Wang et al., 2012) that increase inflammation, and ultimately increase neuroexcitation (Stellwagen D, et al. (2005) J Neurosci 25:3219-3228). There has been no attempt to isolate the signal downstream of TLR4 that is responsible for the adverse effects of opioids.

Soluble Tumor Necrosis Factor (solTNF) is a Key Proinflammatory Product of TLR4 Signaling The present set of experiments tested the hypothesis that TLR4 contributes to morphine tolerance via modulation of inflammatory signaling and glutamate homeostasis in a soluble TNF (solTNF)-dependent manner TNF is a type 1 transmembrane protein that naturally exists in two forms; the more common form, transmembrane TNF (tmTNF), and the less abundant form, soluble TNF which is formed after cleavage of tmTNF by ADAM17/TNF-αlpha Converting Enzyme (TACE), (Kriegler M, et al. (1988) Cell 53:45-53). solTNF signals primarily through TNF receptor 1 (TNFRI), while tmTNF signals through both TNFRI and TNFRII. As TNFRII signaling is protective against glutamate excitotoxicity (Marchetti L, et al. (2004) J Biol Chem 279:32869-32881), and enhanced glutamatergic signaling contributes to opioid tolerance, it wsa predicted that decreasing TNFRI signaling by selectively sequestering solTNF (while preserving TNFRII signaling) would prevent tolerance to morphine. Here, PAG solTNF sequestration was manipulated using a lentivirus and brain-permeant dominant negative TNF (DN-TNF), and the impact on tolerance, cytokine release, and key elements of glutamate homeostasis was examined.

PAG Cytokines and TLR4 mRNA are Increased by Chronic Morphine

Tolerance to morphine developed rapidly. Indeed, systemic administration of one $ED_{50}$ dose of morphine for 3 days is sufficient to induce tolerance as indicated by a 3-fold rightward shift in the morphine dose response curve. Development of morphine tolerance is paralleled by increased gene expression of three major proinflammatory factors in the PAG: TLR4, TNF, and IL-1β, indicating that chronic morphine induces inflammation within the PAG and primes PAG glia to over-respond to subsequent morphine challenges by increasing gene expression of the receptor substrate for opioid-mediated inflammation (TLR4; (Wang X, et al. (2012) Proc Natl Acad Sci USA 109:6325-6330)). Although the increase in vlPAG TNF was not significant in the current study, and is in contrast to what has been noted in the spinal cord (Shen C H, et al. (2011a) Anesth Analg 112:454-459), TNF is found in very low concentration in the CNS (femtomolar to picomolar range), and binds with high affinity to a relatively small number of receptors (Peterson P K, et al. (1998) J Neuroimmunol 83:63-69). In vitro, TNF protein is significantly increased by the TLR4 agonist LPS, in a TACE-dependent manner, 30 minutes following LPS application (von Maltzan K, et al. (2012) PLoS One 7:e29890). In vivo, acute intrathecal morphine analgesia is reduced by TNF within 5 minutes of morphine administration (Hutchinson M R, et al. (2008) Brain Behav Immun 22:1178-1189), suggesting that morphine leads to the quick release of soluble TNF protein via TACE-mediated cleavage of tmTNF. As TNF is primarily responsible for initiating the production of other proinflammatory cytokines (DeLeo J A, et al. (2004) Neuroscientist 10:40-52), morphine signaling through TLR4 may induce rapid cleavage of tmTNF to solTNF protein and stimulate the production of IL-1β3 and TLR4 mRNA to modulate glutamate homeostasis. Findings suggest that TACE inhibition may preserve morphine analgesia and prevent tolerance development in the vlPAG by preventing TLR4-mediated soluble TNF signaling. The PAG, along with the RVM and spinal cord, form the descending pain modulatory circuit, and all three regions are critical neural substrates for the analgesic effects of morphine. In the present study, a focus was placed on TLR4 mediated neuroinflammation within the PAG, however similar neuroinflammatory spinal cord responses have been implicated in the development of morphine tolerance (Raghavendra V, et al. (2002) J Neurosci 22:9980-9989).

Inhibition of solTNF Prevents Tolerance to Morphine

Systemically administered XPro®1595 was efficiently transported to midbrain tissue, and normalized vlPAG TNF, IL-1β, and TLR4 mRNA levels, effectively preserving morphine efficacy following chronic exposure. These data are the first to establish a role for TNF in opiate tolerance, and are the first to identify solTNF as a critical proinflammatory factor mediating opioid tolerance development. Currently there are FDA-approved non-selective biological inhibitors that sequester both forms of TNF (solTNF and tmTNF), but these drugs have been associated with neurological deficits and demyelinating disease in patients who were previously neurologically normal (Seror R, et al. (2013) Rheumatology (Oxford) 52:868-874), indicating the critical need to differentiate the actions of the two TNF isoforms.

PAG solTNF signaling is necessary for changes in mRNA induced by chronic systemic morphine or PAG LPS Morphine tolerance, induced by systemic morphine administration, decreased astrocytic (GLT-1 and GLAST), but not neuronal (EAACI), glutamate transporter mRNA in the vlPAG, complementing our previous findings (Eidson L N, et al. (2013) J Neurosci 33:15952-15963), and a vast literature demonstrating a role for glia (Watkins L R, et al. (2005) Trends Neurosci 28:661-669) and excitatory neurotransmission (McLemore G L, et al. (1997) Brain Res 778:120-126) in morphine tolerance. Astrocytes are responsible for the majority of glutamate uptake in the CNS via GLT-1 and GLAST (Rothstein J D, et al. (1996) Neuron 16:675-686), thereby terminating glutamatergic signaling (Kanai Y, et al. (1993) Trends Neurosci 16:365-370). A significant increase in CSF glutamate and aspartate has been reported in morphine-tolerant humans (Wong C S, et al. (2002) Can J Anaesth 49:561-565), and morphine challenge increases glutamate in the CSF of morphine tolerant rats (Tai Y H, et al. (2006) Pain 124:77-86). Increased glutamate uptake by GLT-1 attenuates morphine tolerance in mice (Nakagawa T, et al. (2001) Eur J Pharmacol 419:39-45). These data suggest that a breakdown in astrocyte-mediated glutamate homeostasis significantly contributes to opioid tolerance. Chronic vlPAG LPS resulted in behavioral and molecular phenotypes that paralleled morphine-treated rats, suggesting that TLR4 signaling in the PAG opposes morphine analgesia by promoting neuroinflammation and disrupting the main source of glutamate reuptake in the central nervous system. Sequestration of vlPAG solTNF normalized the morphine and endotoxin-induced changes in glutamate transporter mRNA and prevented morphine tolerance, suggesting that solTNF signaling mediates the effects of TLR4.

A Proposed Inflammatory Model of Morphine Tolerance

Figure 5:
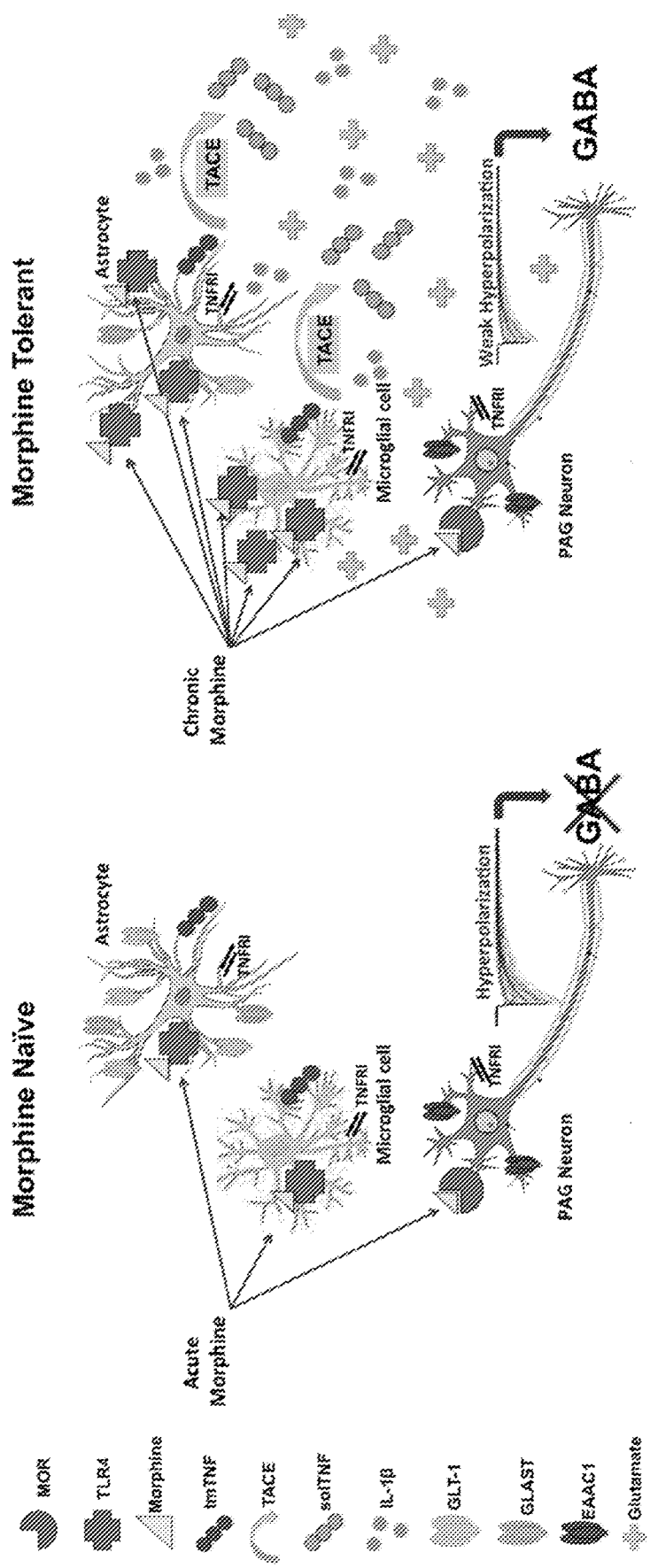
FIG. 5 is a schematic diagram illustrating our hypothesized model of solTNF-induced morphine tolerance development in the PAG Based on the major conclusions of our own data and the data of others, we hypothesize that chronic morphine binds to vlPAG TLR4 and leads to cleavage of transmembrane TNF (tmTNF) to soluble TNF (solTNF) by TNF converting enzyme (TACE) to increase proinflammatory gene expression (TLR4, IL-1β) and decrease astrocytic glutamate transporter mRNA (GLT-1 and GLAST) in the vlPAG. These changes effectively increase the availability of glutamate in the synapse, thereby decreasing the ability of morphine to hyperpolarize GABAergic neurons. These changes associated with morphine tolerance prevent morphine from initiating signaling through the descending analgesic circuit.

Morphine and other opioids bind to neuronal mu opioid receptors (MOR) (Pasternak G W, et al. (2013) Pharmacol Rev 65:1257-1317) and elicit analgesia, in part, by hyperpolarization of GABAergic neurons (Basbaum A I, et al. (1978) Ann Neurol 4:451-462; Lau B K, et al. (2014) Curr Opin Neurobiol 29C:159-164). Indeed, opioids have a direct inhibitory effect on most MOR expressing neurons (Vaughan C W, et al. (1997) Nature 390:611-614) including those in the descending analgesic circuit (e.g., PAG) (Vaughan C W, et al. (1997) Nature 390:611-614). Based on current findings, it is propose that morphine binds to neuronal MOR as well as glial TLR4 in the PAG, and that concurrent activity at these receptors modulates the analgesic efficacy of morphine via two opposing mechanisms: (1) opiate binding at MOR results in hyperpolarization of GABAergic neurons and induction of opiate analgesia; and (2) opiate binding at glial TLR4 leads to increased vlPAG solTNF signaling that simultaneously promotes inflammation and disrupts the ability of astrocytes to scavenge excess glutamate, counteracting MOR-mediated hyperpolarization of GABAergic neurons to promote morphine tolerance. Key tenants of the proposed model are illustrated in FIG. 5.

Conclusions

The disclosed results support the use of solTNF sequestration peptides such as XPro®1595 as a potential adjunct to opioid therapy. As transmembrane TNF is the TNF ligand that signals through TNFRII in physiological conditions, and TNFRII is protective against glutamate excitotoxicity (Marchetti L, et al. (2004) J Biol Chem 279:32869-32881), anti-solTNF treatment is likely to be a dually beneficial countermeasure to the opioid-induced neuroexcitability known to contribute to tolerance (Trujillo K A, et al. (1991) Science 251:85-87; McLemore G L, et al. (1997) Brain Res 778:120-126). As the mechanisms underlying hyperalgesia (DeLeo J A, et al. (2004) Neuroscientist 10:40-52) are strikingly similar to the mechanisms underlying opioid tolerance development, these data suggest that selective anti-solTNF biologics could complement opioid therapy in the clinic by suppressing nociceptive signals at the site of injury and in the spinal cord, as well as preserving morphine analgesic efficacy by preventing vlPAG glia activation.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating morphine tolerance and/or symptoms associated therewith comprising administering a therapeutically effective amount of a dominant negative TNF-α polypeptide to a subject in need thereof, whereby said symptoms are improved in said subject.

2. The method of claim 1, wherein said dominant negative TNF-α polypeptide comprises a variant sequence relative to wild-type TNF-α.

3. The method of claim 2, wherein said variant comprises the amino acid substitutions A145R/I97T or V1M/R31C/C69V/Y87H/C101A/A145R relative to wild-type human TNF-α sequence, wherein the wild-type human TNF-α sequence comprises SEQ ID NO:3.

4. The method of claim 1, wherein said dominant negative TNF-α polypeptide inhibits soluble TNF-α but does not inhibit signaling by transmembrane TNF-α.

5. The method of claim 4, wherein said dominant negative TNF-α polypeptide is PEGylated.

6. The method of claim 4, wherein said dominant negative TNF-α polypeptide is XPro1595.

7. The method of claim 1, wherein symptoms are improved to a greater extent when said dominant negative TNF-α polypeptide, than when a non-selective inhibitor of TNF-α is administered.

8. A method of increasing glutamate uptake in a patient in need thereof comprising administering to said patient a dominant negative TNF-α polypeptide, whereby glutamate uptake is increased as compared to glutamate uptake prior to said administration.

9. The method of claim 8, wherein said patient exhibits morphine tolerance prior to said administration and reduced morphine tolerance following said administration.

* * * * *